United States Patent [19]
Plyley et al.

[11] Patent Number: 5,706,998
[45] Date of Patent: Jan. 13, 1998

[54] SURGICAL STAPLER WITH ALIGNMENT PIN LOCKING MECHANISM

[75] Inventors: Alan K. Plyley, Goleta; Claude A. Vidal, Santa Barbara; Russell J. Redmond, Goleta, all of Calif.

[73] Assignee: United States Surgical Corporation, Norwalk, Conn.

[21] Appl. No.: 503,129

[22] Filed: Jul. 17, 1995

[51] Int. Cl.⁶ .................................................. A61B 17/068
[52] U.S. Cl. ................ 227/175.3; 227/19; 227/175.2; 227/176.1
[58] Field of Search .................. 227/175.1, 175.2, 227/175.3, 175.4, 176.1, 19

[56] References Cited

U.S. PATENT DOCUMENTS

| | | |
|---|---|---|
| Re. 34,519 | 1/1994 | Fox et al. . |
| D. 283,733 | 5/1986 | Rawson et al. . |
| 2,174,219 | 9/1939 | Balma . |
| 2,246,647 | 6/1941 | Vancura . |
| 3,079,606 | 3/1963 | Bobrov et al. . |
| 3,079,608 | 3/1963 | Babkin . |
| 3,080,564 | 3/1963 | Strekopytov et al. . |
| 3,252,643 | 5/1966 | Strekopytov et al. . |
| 3,490,675 | 1/1970 | Green et al. . |
| 3,499,591 | 3/1970 | Green . |
| 3,675,688 | 7/1972 | Bryan et al. . |
| 3,844,289 | 10/1974 | Noiles . |
| 4,086,926 | 5/1978 | Green et al. . |
| 4,202,480 | 5/1980 | Annett . |
| 4,256,251 | 3/1981 | Moshofsky . |
| 4,304,236 | 12/1981 | Conta et al. . |
| 4,331,276 | 5/1982 | Bourque . |
| 4,354,628 | 10/1982 | Green . |
| 4,391,401 | 7/1983 | Moshofsky . |
| 4,473,077 | 9/1984 | Noiles et al. . |
| 4,480,640 | 11/1984 | Becht . |
| 4,500,025 | 2/1985 | Skwor . |
| 4,513,746 | 4/1985 | Aranyi et al. . |
| 4,519,532 | 5/1985 | Foslien . |
| 4,520,817 | 6/1985 | Green . |
| 4,522,327 | 6/1985 | Korthoff et al. . |
| 4,523,695 | 6/1985 | Braun et al. . |
| 4,527,724 | 7/1985 | Chow et al. . |
| 4,540,110 | 9/1985 | Bent et al. . |
| 4,566,620 | 1/1986 | Green et al. . |
| 4,569,346 | 2/1986 | Poirier . |
| 4,573,622 | 3/1986 | Green et al. . |
| 4,576,167 | 3/1986 | Noils . |
| 4,580,712 | 4/1986 | Green . |
| 4,585,153 | 4/1986 | Failla et al. . |
| 4,591,085 | 5/1986 | Di Giovanni . |

(List continued on next page.)

FOREIGN PATENT DOCUMENTS

| | | |
|---|---|---|
| 2542188 | 9/1984 | European Pat. Off. . |
| 0136950 | 4/1985 | European Pat. Off. . |
| 0220029 | 4/1987 | European Pat. Off. . |
| 0273468 | 7/1988 | European Pat. Off. . |
| 0537571 | 4/1993 | European Pat. Off. . |
| 2141066 | 12/1984 | United Kingdom . |

OTHER PUBLICATIONS

"Auto Sutur® POLY CS™-57 Disposable Surgical Stapler", United States Surgical Corporation, 1988.

"Proximate RL Plus Reloadable Linear Stapler", Ethicon, Inc., 1990.

*Primary Examiner*—Scott A. Smith

[57] ABSTRACT

A surgical stapler having a supporting frame, including a stationary jaw having an anvil, a movable jaw, a replaceable staple cartridge carried by the movable jaw, a mechanism for approximating the cartridge relative to the anvil, and a mechanism for firing the device so as to crimp the staples against the anvil in a manner to enable the surgeon to substantially simultaneously place one or more rows of surgical staples in organs or tissues. The device includes interrelated, cooperating first and second locking mechanisms for positively preventing refiring if the staple cartridge is spent and for providing a tactile sensation to the surgeon to indicate that a spent staple cartridge is present within the instrument.

37 Claims, 16 Drawing Sheets

U.S. PATENT DOCUMENTS

| | | |
|---|---|---|
| 4,592,498 | 6/1986 | Braun et al. . |
| 4,597,517 | 7/1986 | Wagdy . |
| 4,605,004 | 8/1986 | Di Giovanni et al. . |
| 4,610,383 | 9/1986 | Rothfuss et al. . |
| 4,633,861 | 1/1987 | Chow et al. . |
| 4,635,634 | 1/1987 | Santos . |
| 4,646,745 | 3/1987 | Noiles . |
| 4,664,305 | 5/1987 | Blake, III et al. . |
| 4,665,916 | 5/1987 | Green . |
| 4,684,051 | 8/1987 | Akopov et al. . |
| 4,714,187 | 12/1987 | Green . |
| 4,715,520 | 12/1987 | Roehr, Jr. et al. . |
| 4,728,020 | 3/1988 | Green et al. . |
| 4,741,336 | 5/1988 | Failla et al. . |
| 4,788,978 | 12/1988 | Strekopytov et al. . |
| 4,807,628 | 2/1989 | Peters et al. . |
| 4,809,898 | 3/1989 | Gassner et al. . |
| 4,821,942 | 4/1989 | Richards et al. . |
| 4,848,637 | 7/1989 | Pruitt . |
| 4,850,355 | 7/1989 | Brooks et al. . |
| 4,869,414 | 9/1989 | Green et al. . |
| 4,869,415 | 9/1989 | Fox ............................................. 227/19 |
| 4,881,545 | 11/1989 | Isaacs et al. . |
| 4,892,244 | 1/1990 | Fox et al. . |
| 4,915,100 | 4/1990 | Green . |
| 4,930,503 | 6/1990 | Pruitt . |
| 4,938,408 | 7/1990 | Bedi et al. . |
| 4,941,623 | 7/1990 | Pruitt . |
| 4,955,959 | 9/1990 | Tompkins et al. . |
| 4,964,559 | 10/1990 | Deniega et al. . |
| 5,018,657 | 5/1991 | Pedlick et al. . |
| 5,027,834 | 7/1991 | Pruitt . |
| 5,031,814 | 7/1991 | Tompkins et al. . |
| 5,071,052 | 12/1991 | Rodak et al. . |
| 5,100,042 | 3/1992 | Gravener et al. . |
| 5,116,349 | 5/1992 | Aranyi . |
| 5,137,198 | 8/1992 | Nobis et al. . |
| 5,190,203 | 3/1993 | Rodak . |
| 5,275,323 | 1/1994 | Schulze et al. ..................... 227/176.1 |
| 5,413,267 | 5/1995 | Solyntjes et al. . |
| 5,458,279 | 10/1995 | Plyley . |
| 5,470,006 | 11/1995 | Rodak . |
| 5,470,008 | 11/1995 | Rokdak . |
| 5,470,009 | 11/1995 | Rodak . |
| 5,509,596 | 4/1996 | Green et al. . |
| 5,579,978 | 12/1996 | Green et al. ........................ 227/175.3 |
| 5,580,067 | 12/1996 | Hamblin ............................. 227/175.2 |

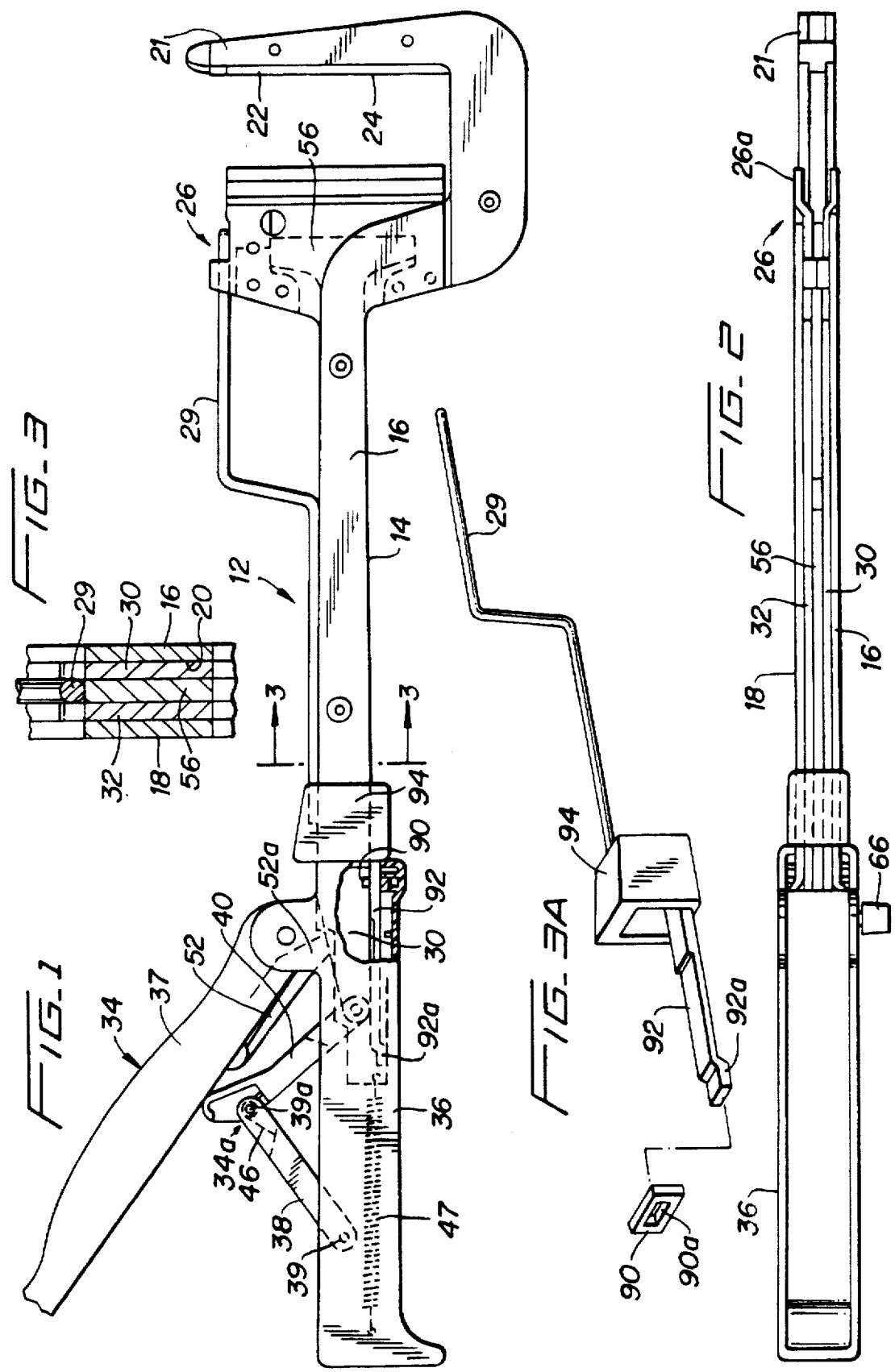

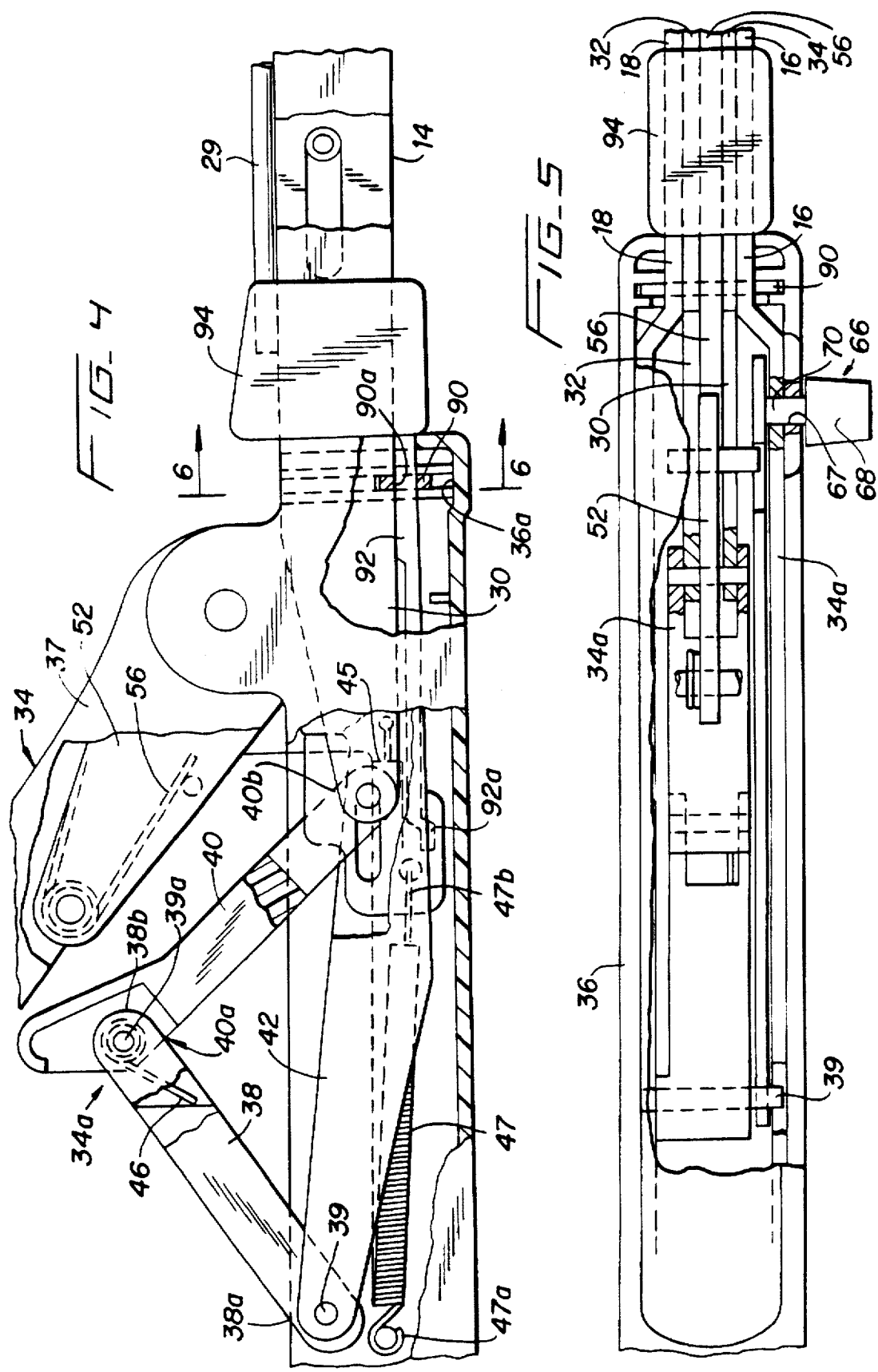

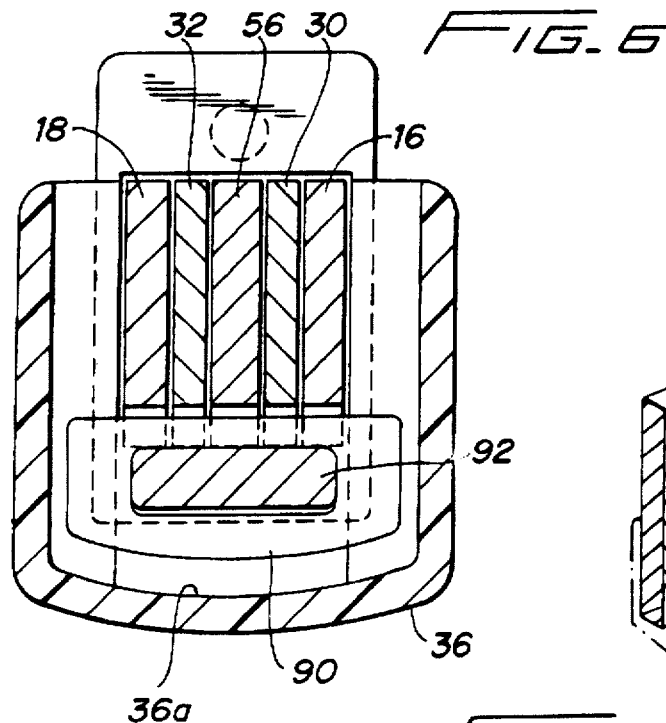
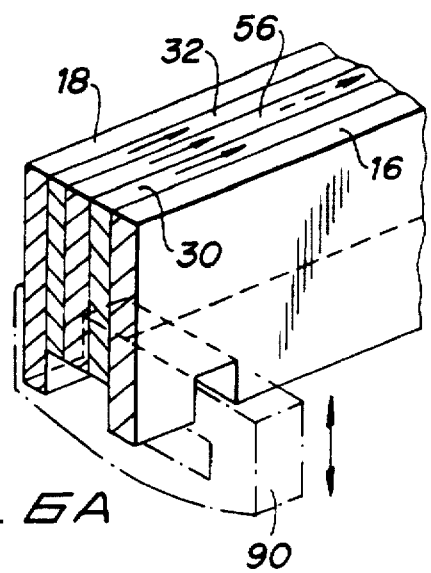
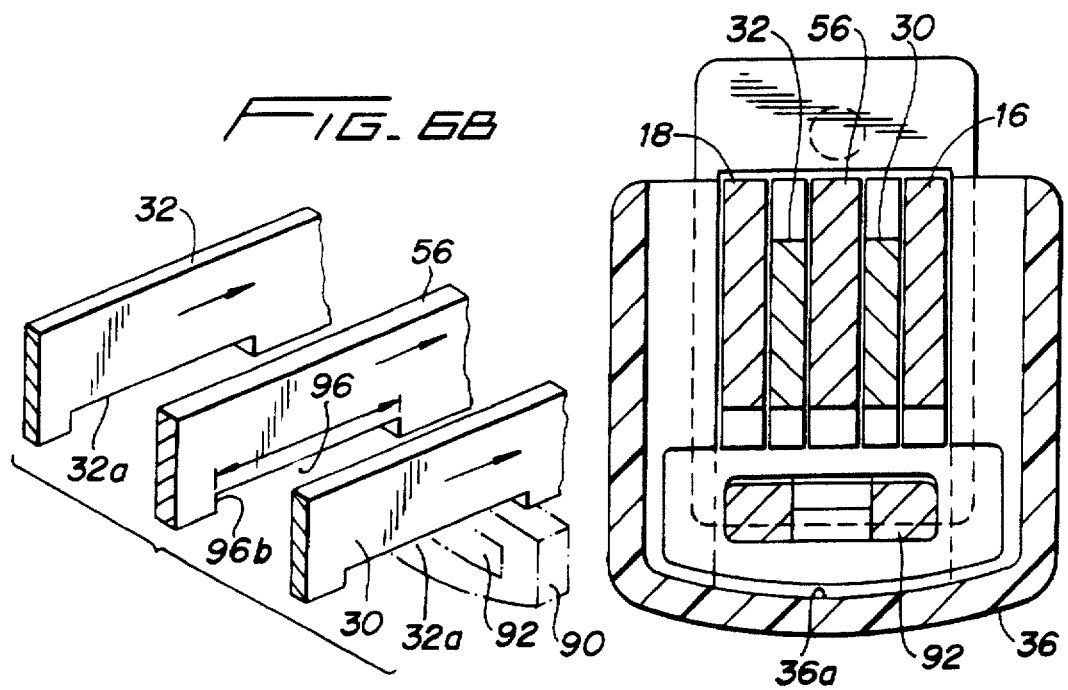

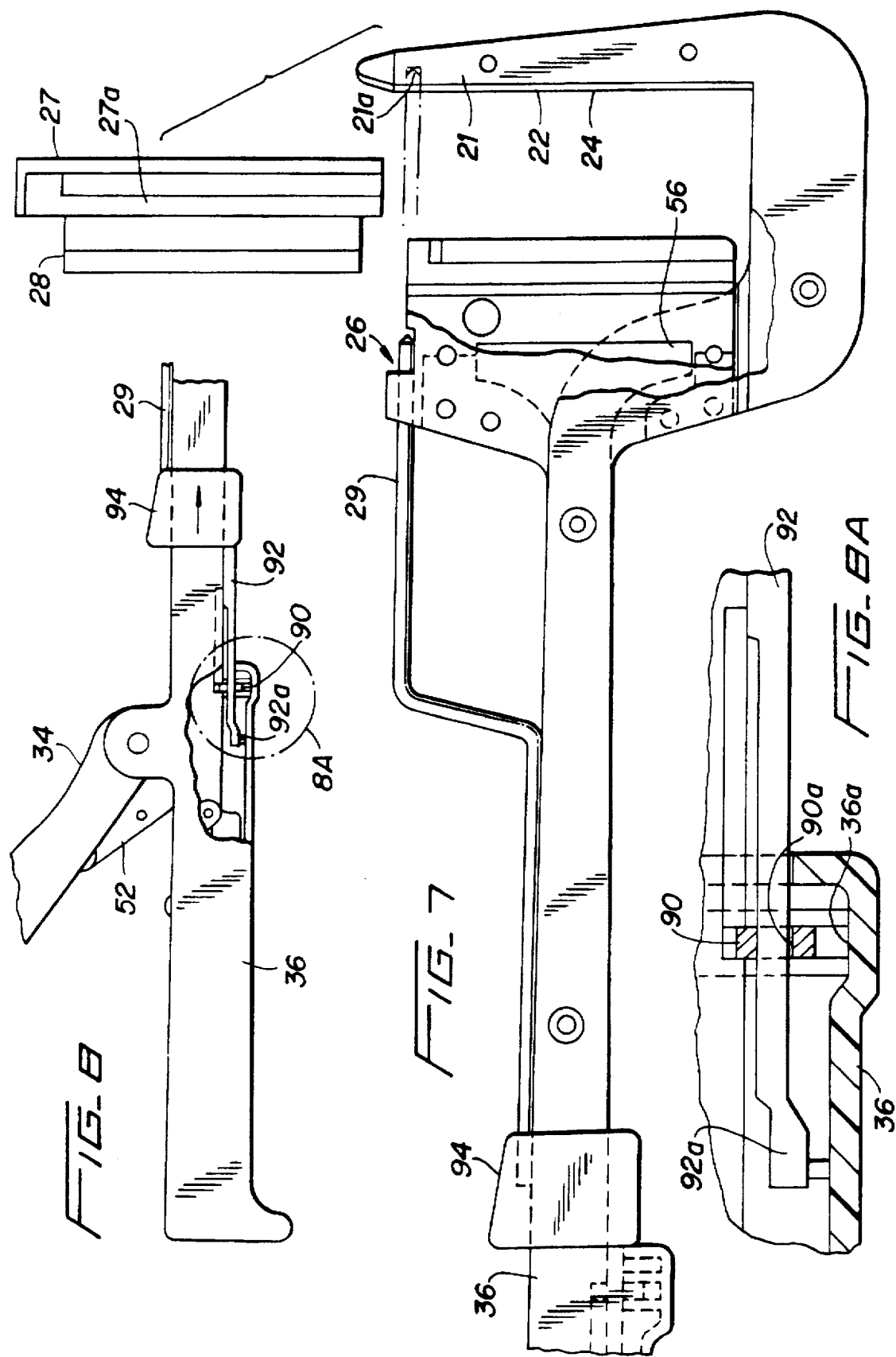

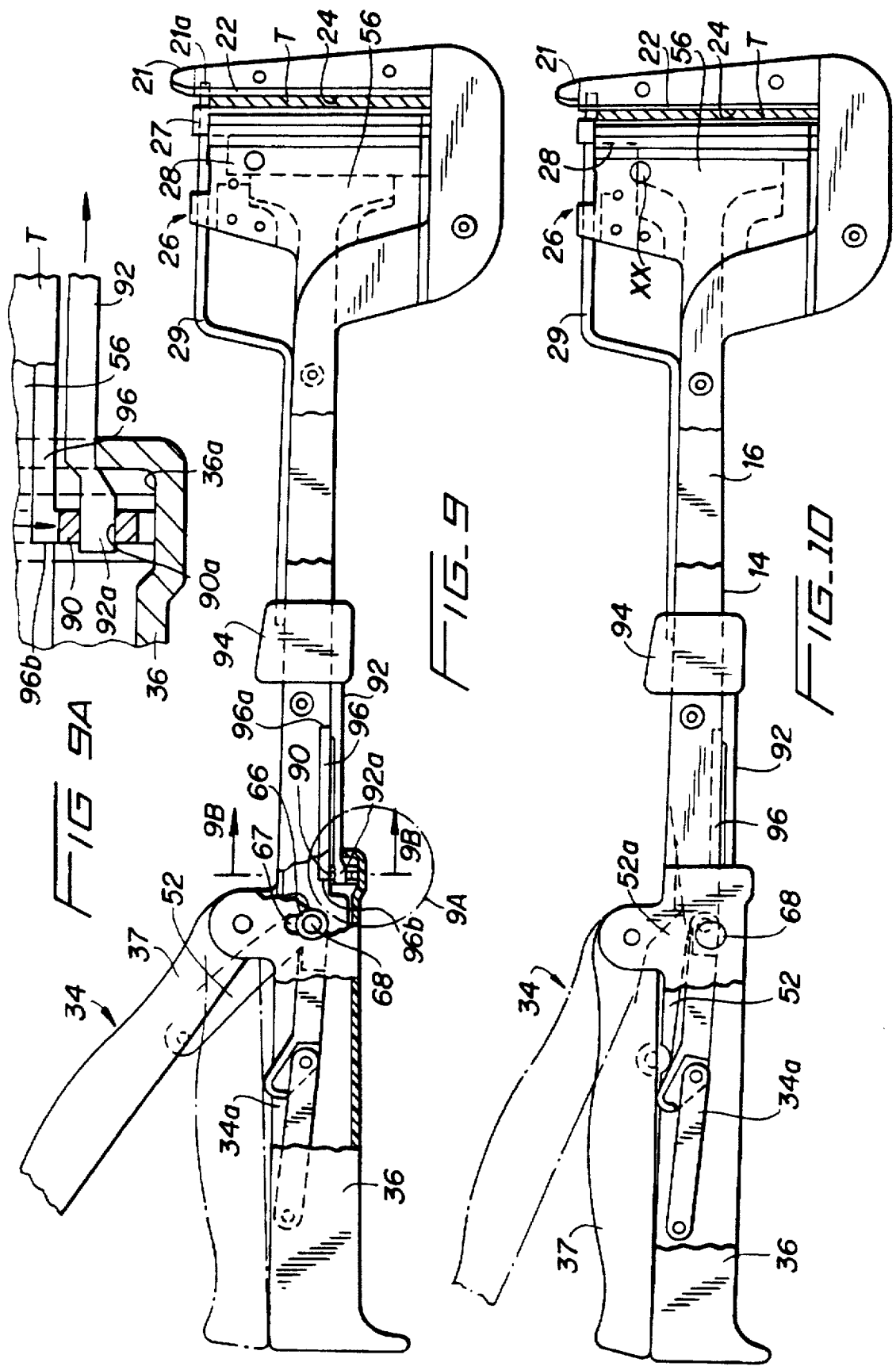

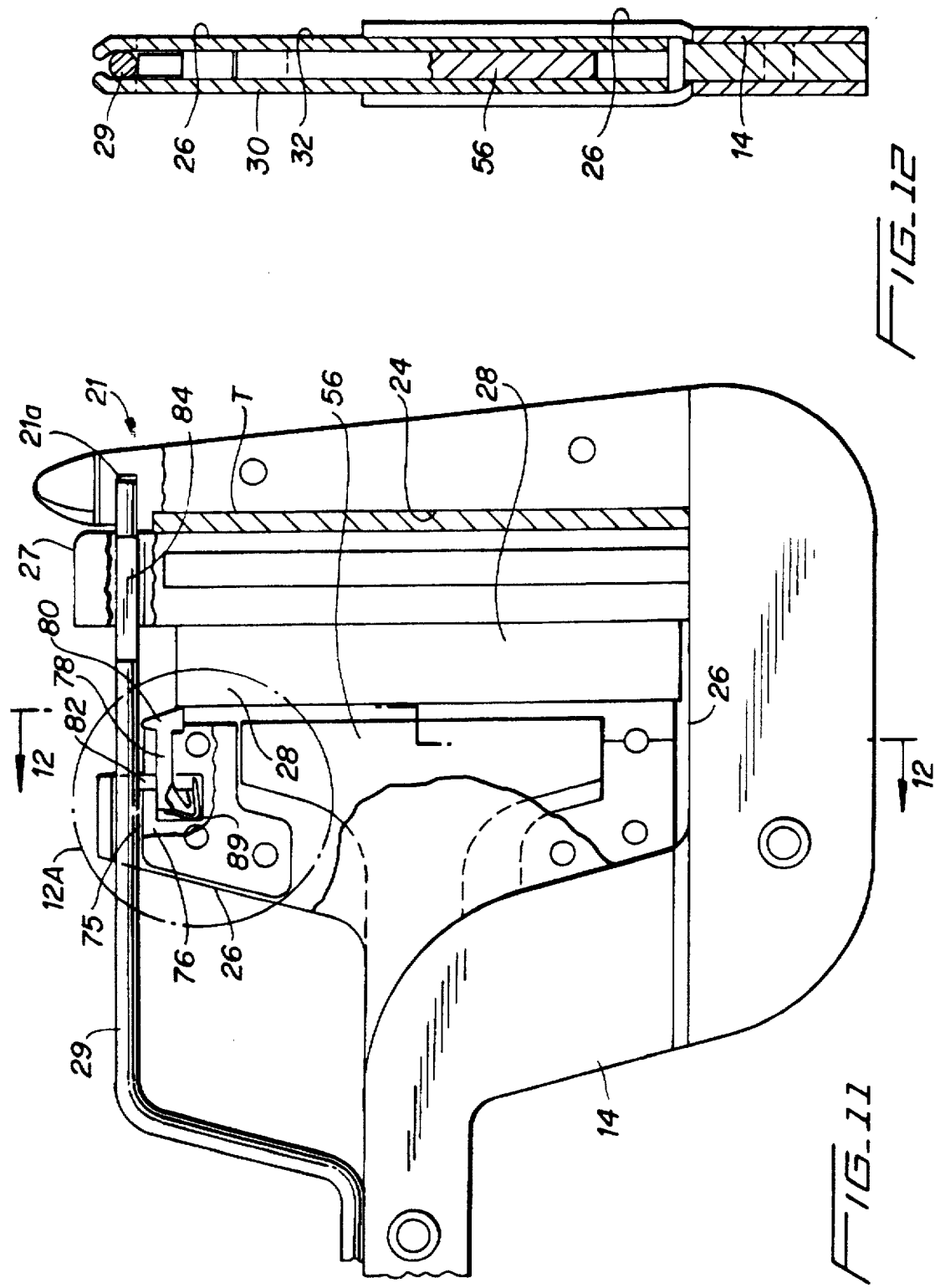

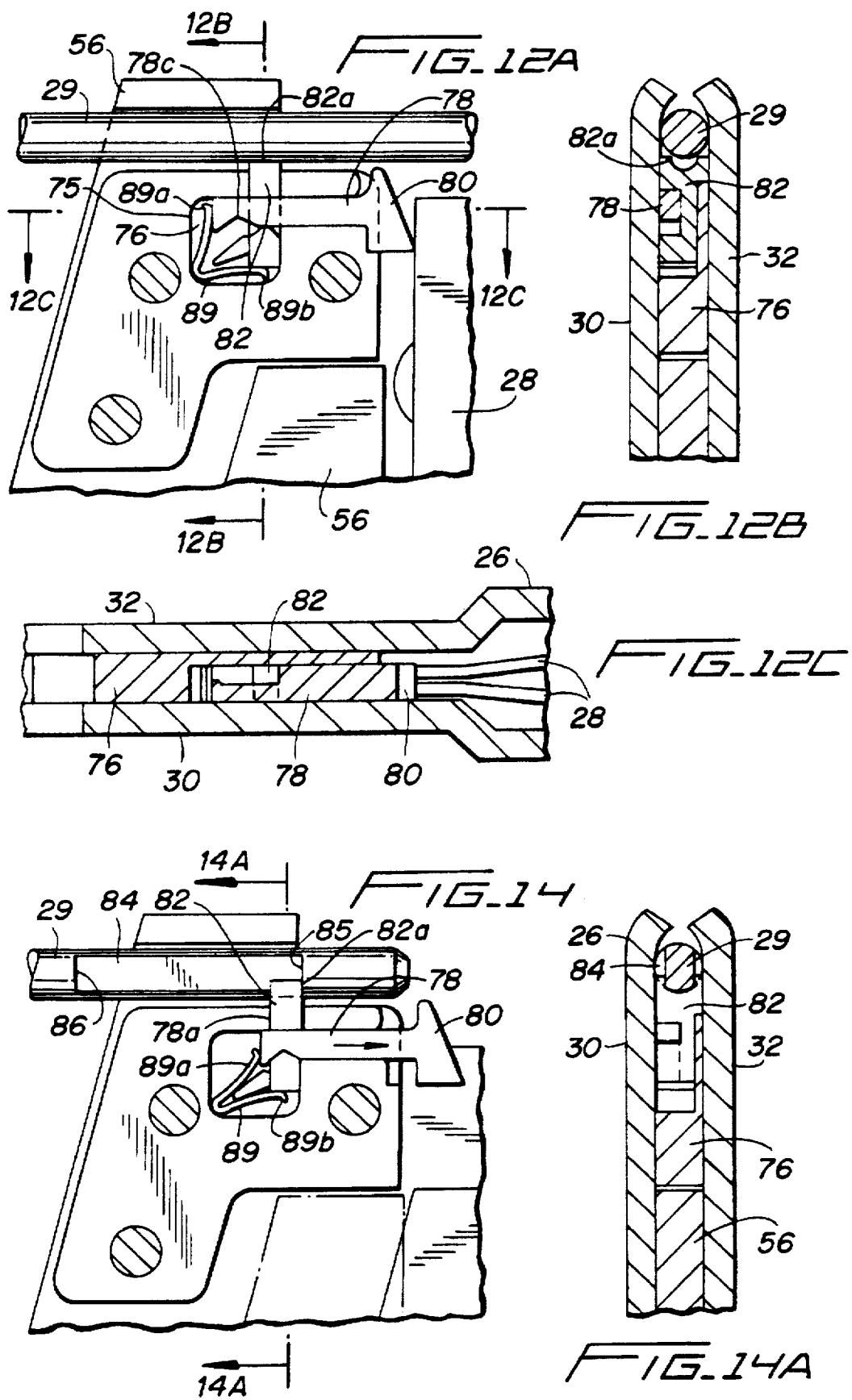

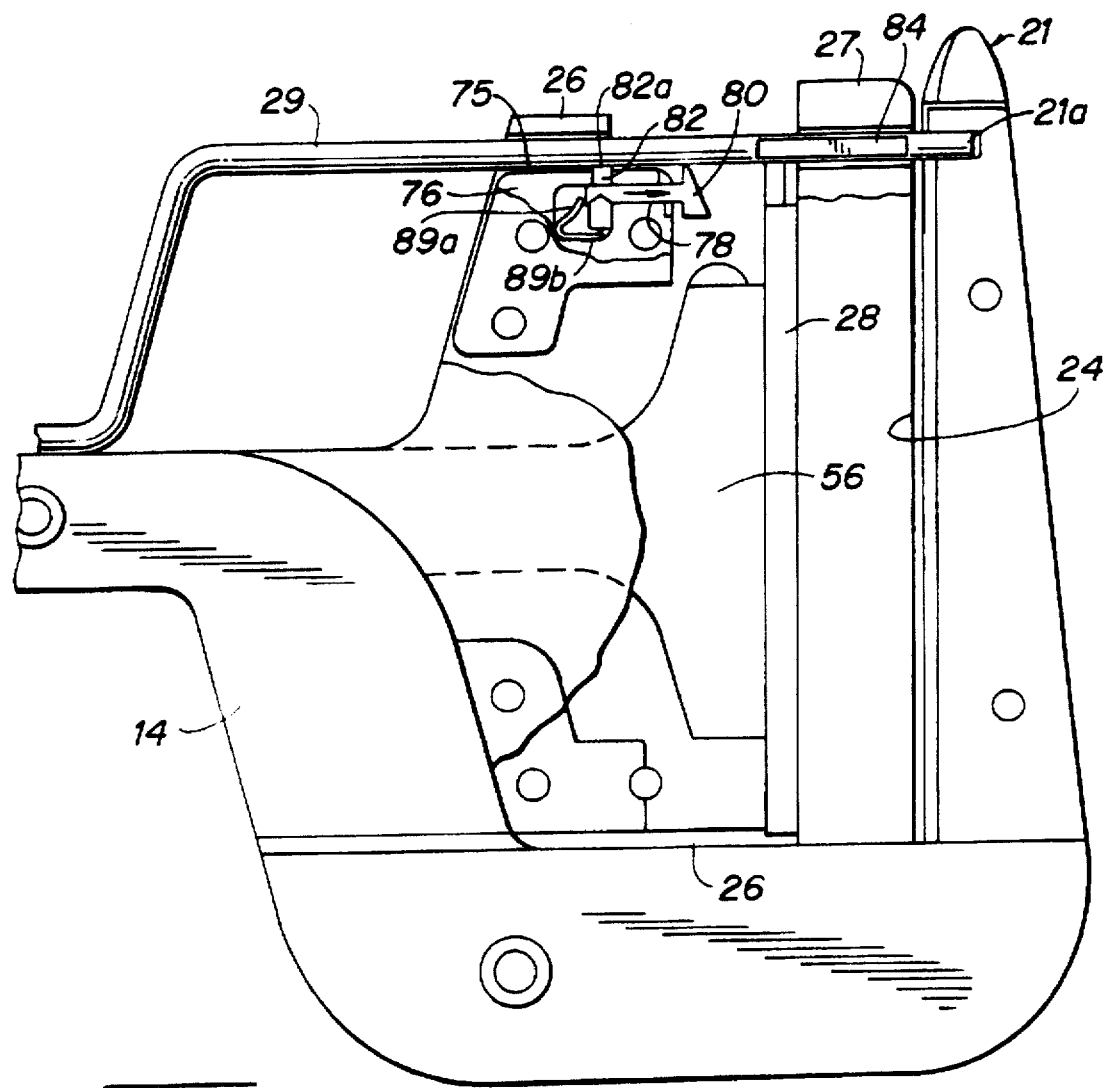
FIG_13
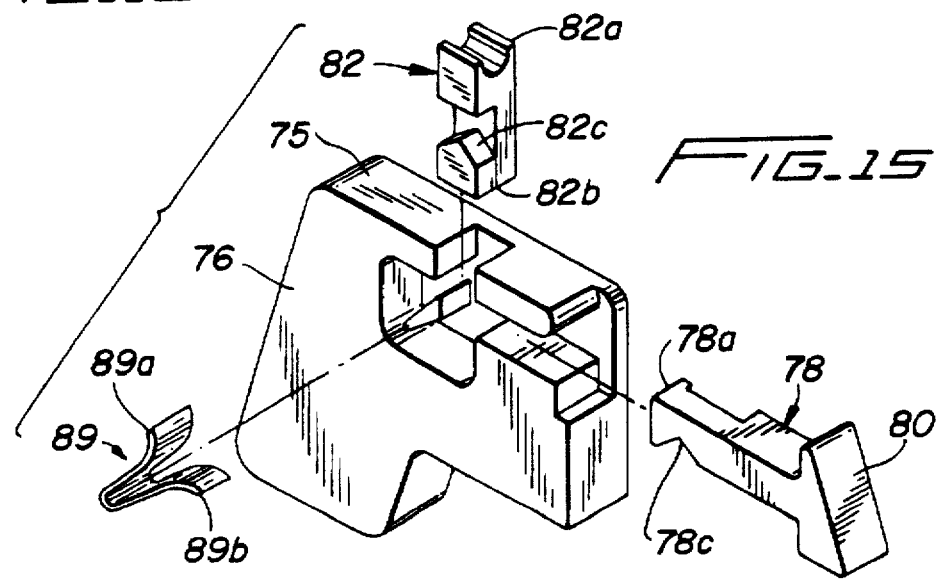
FIG_15

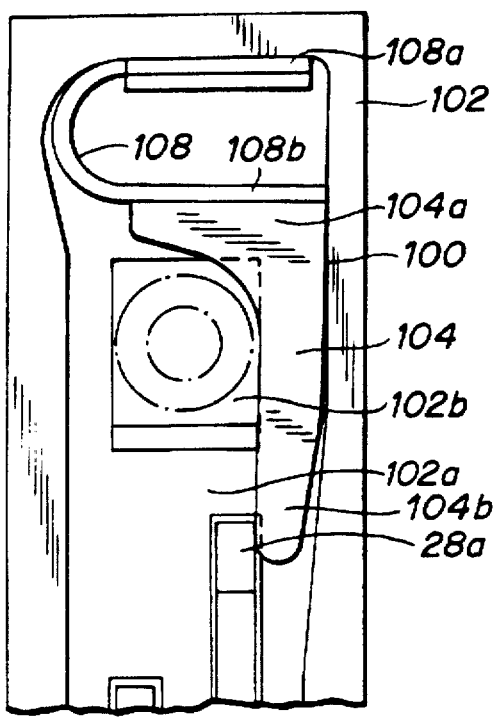
FIG._16
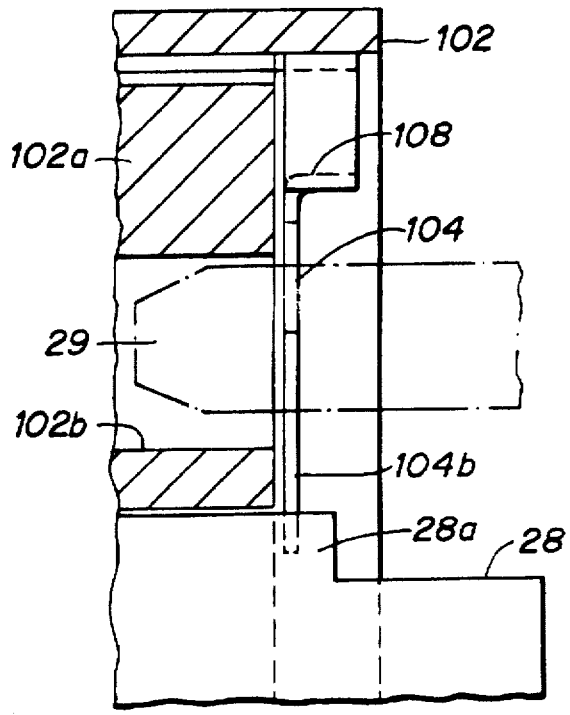
FIG._17
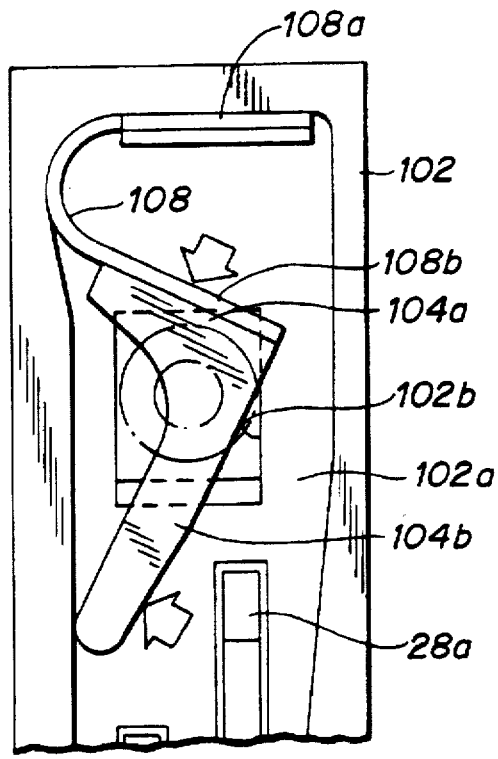
FIG._18
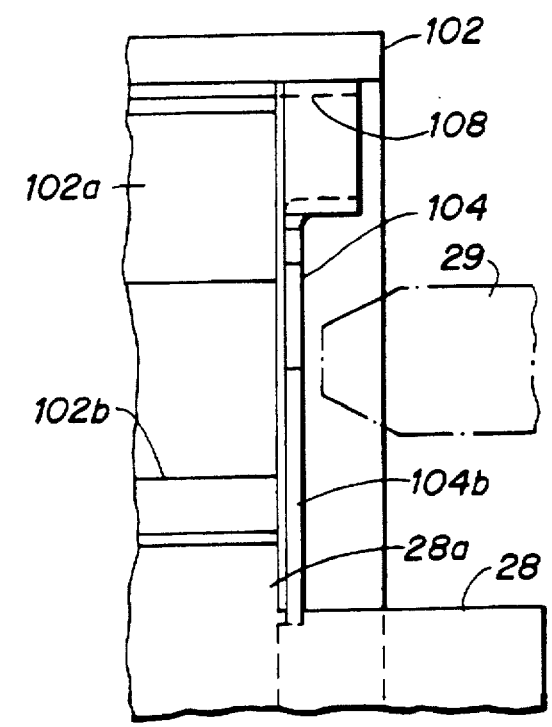
FIG._19

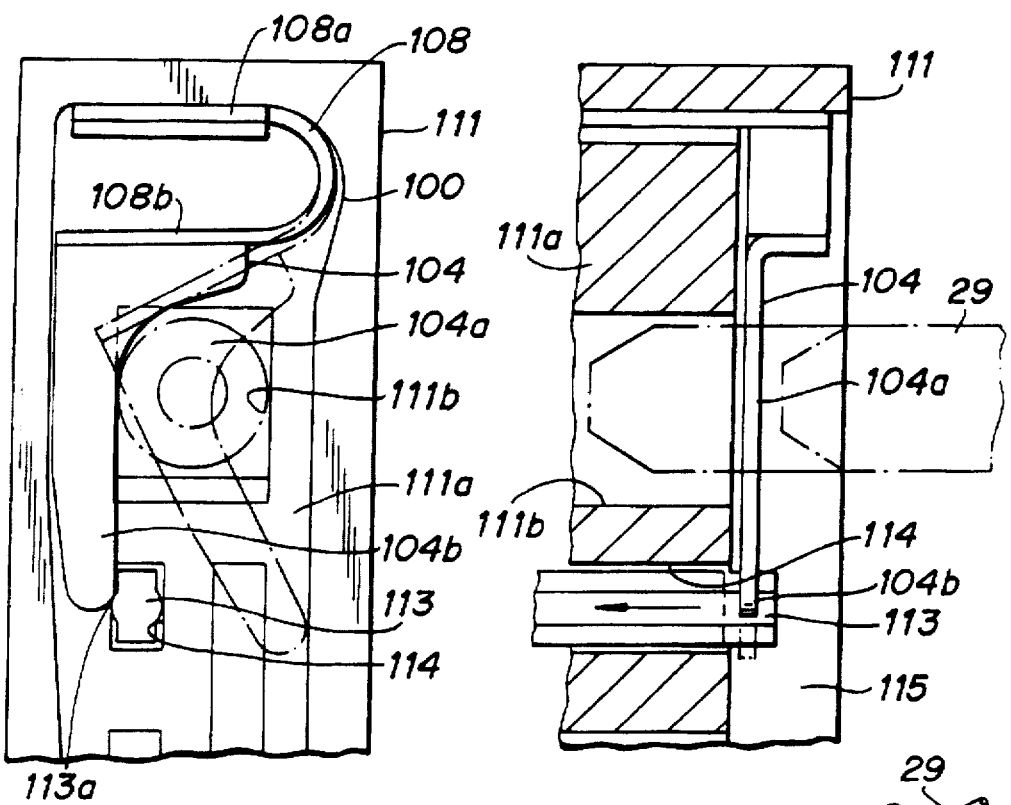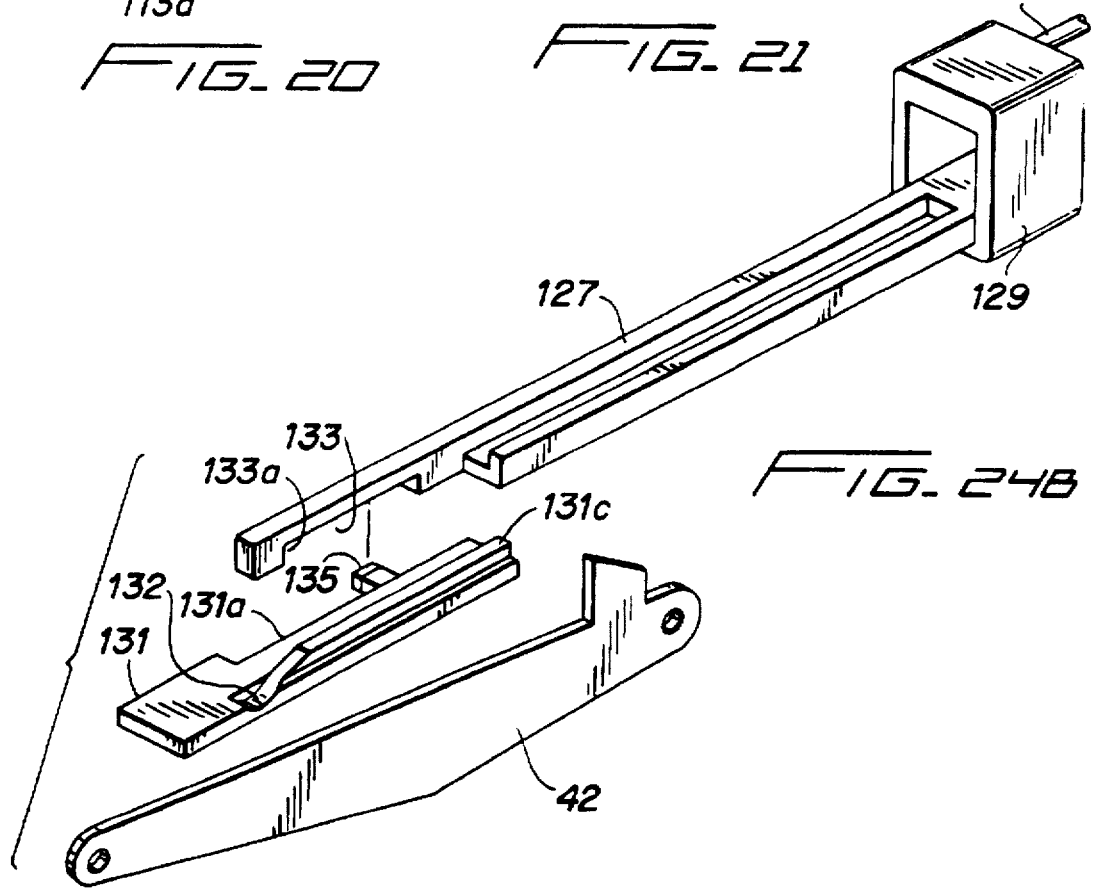

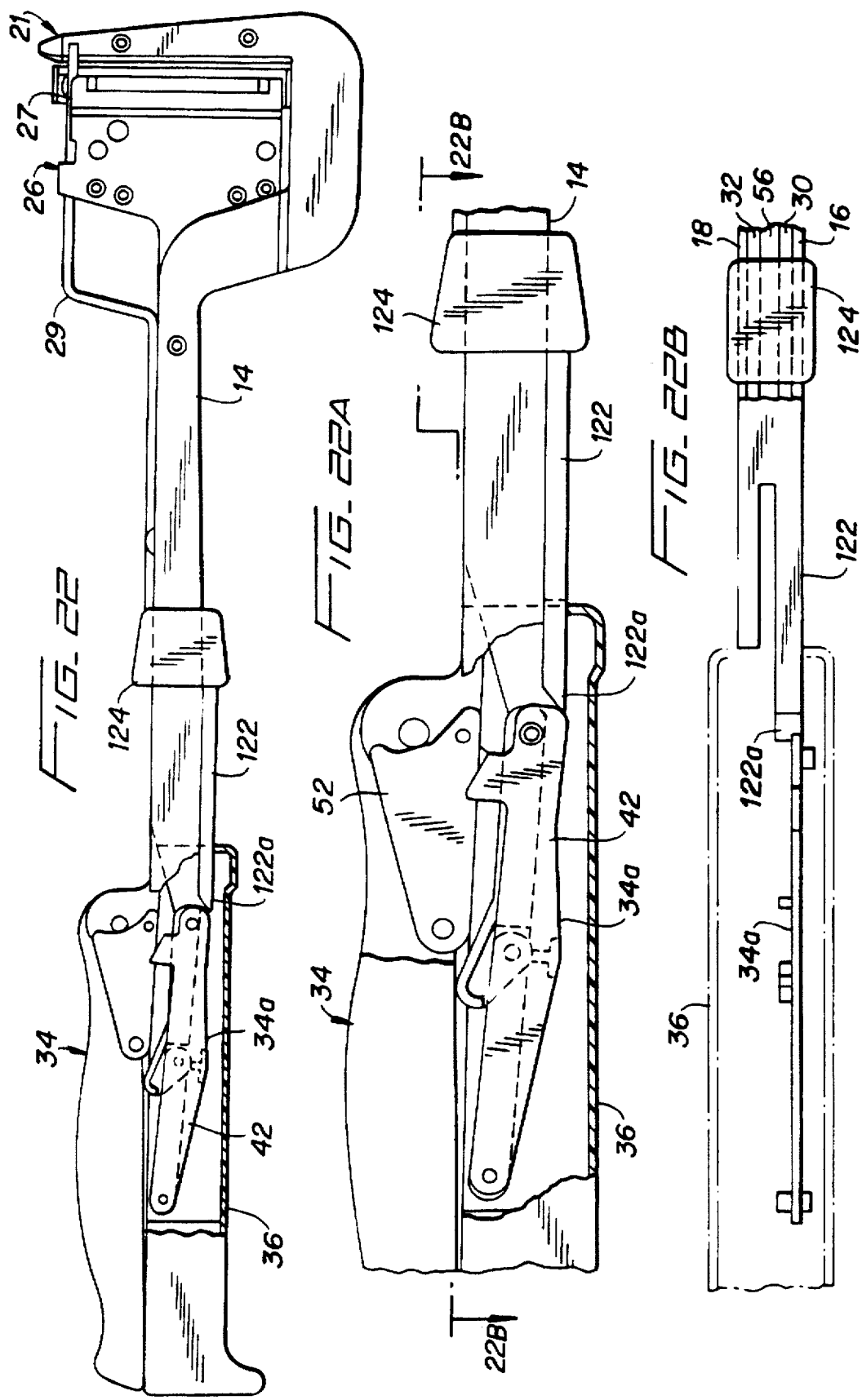

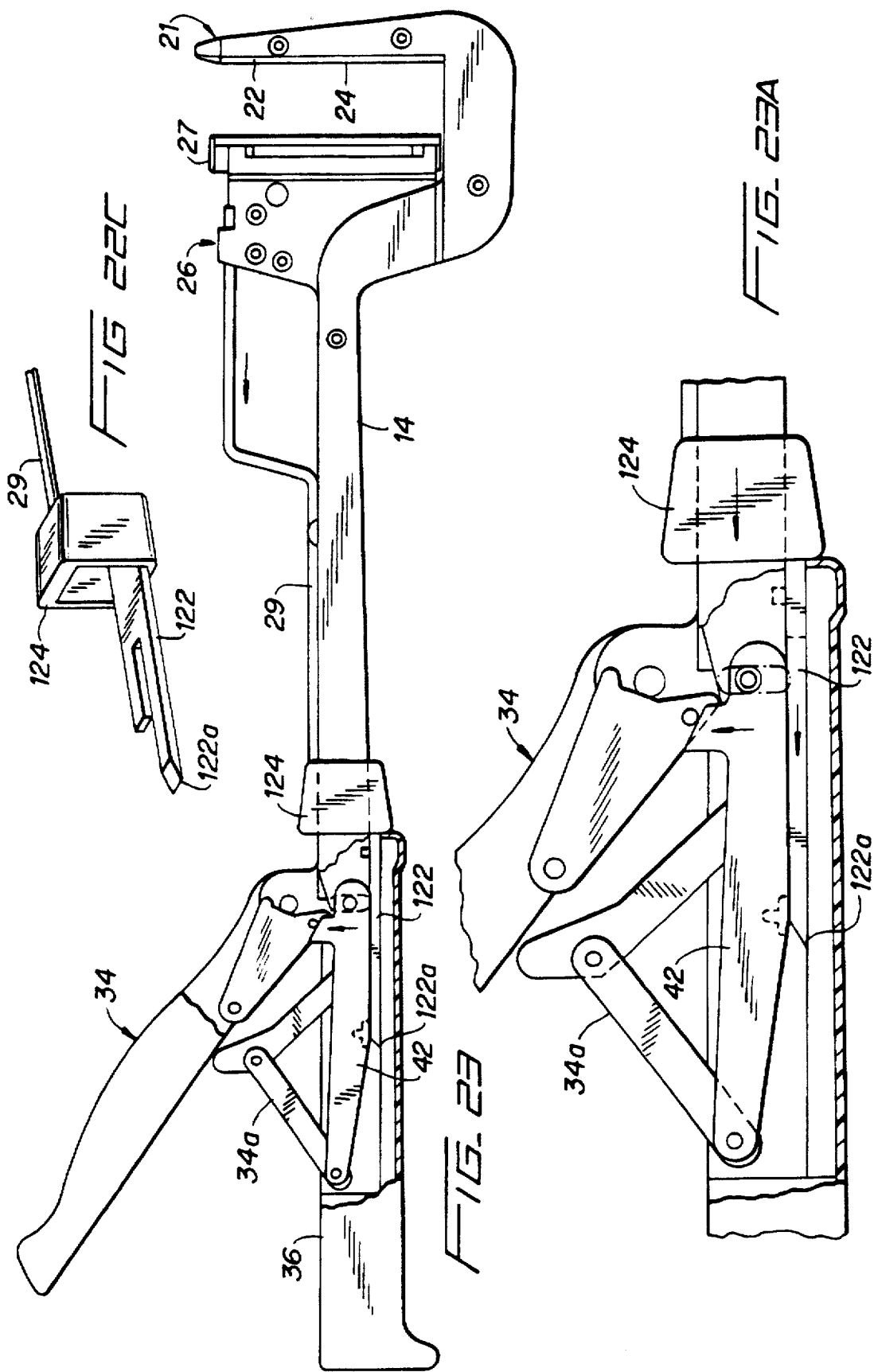

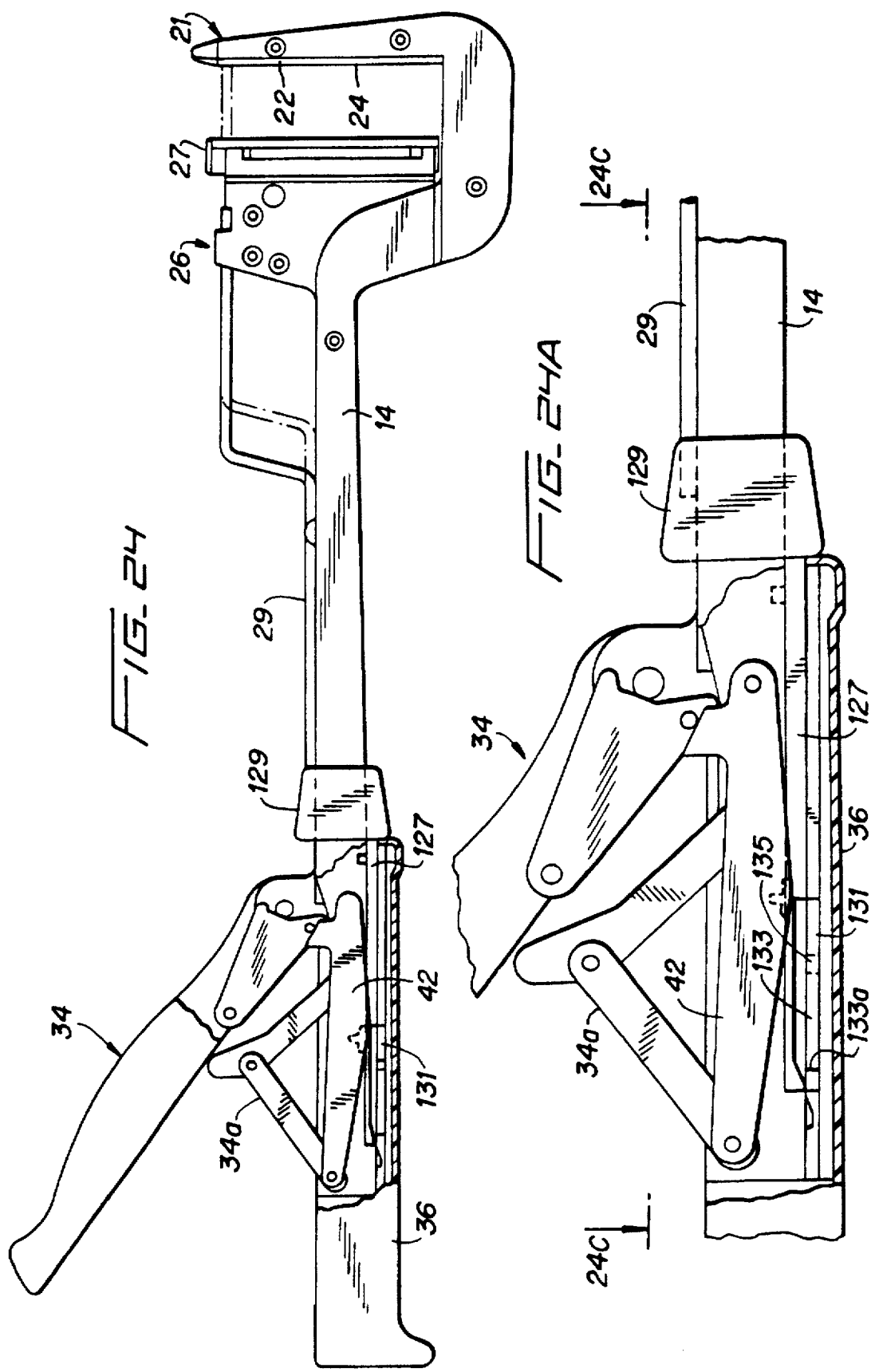

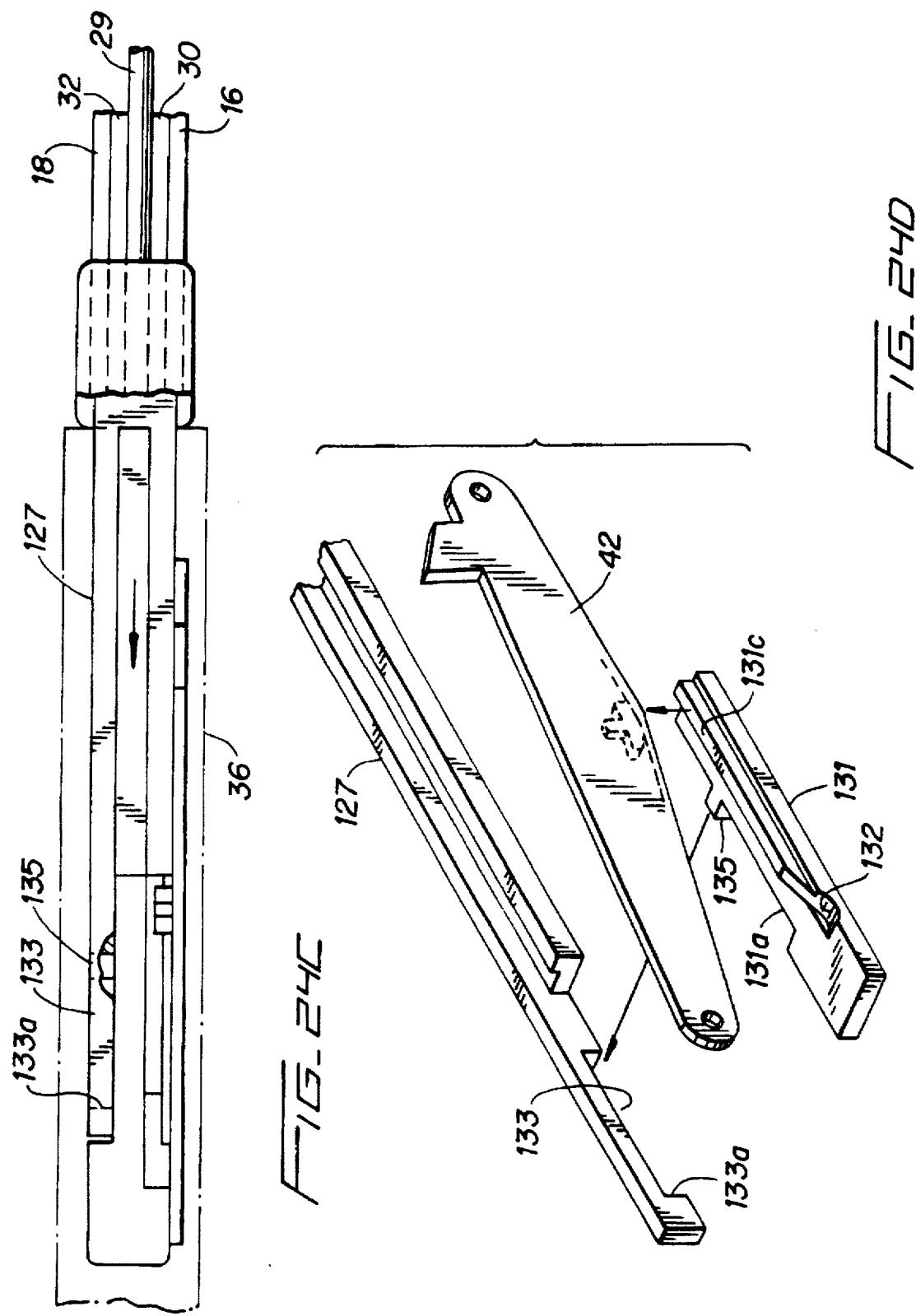

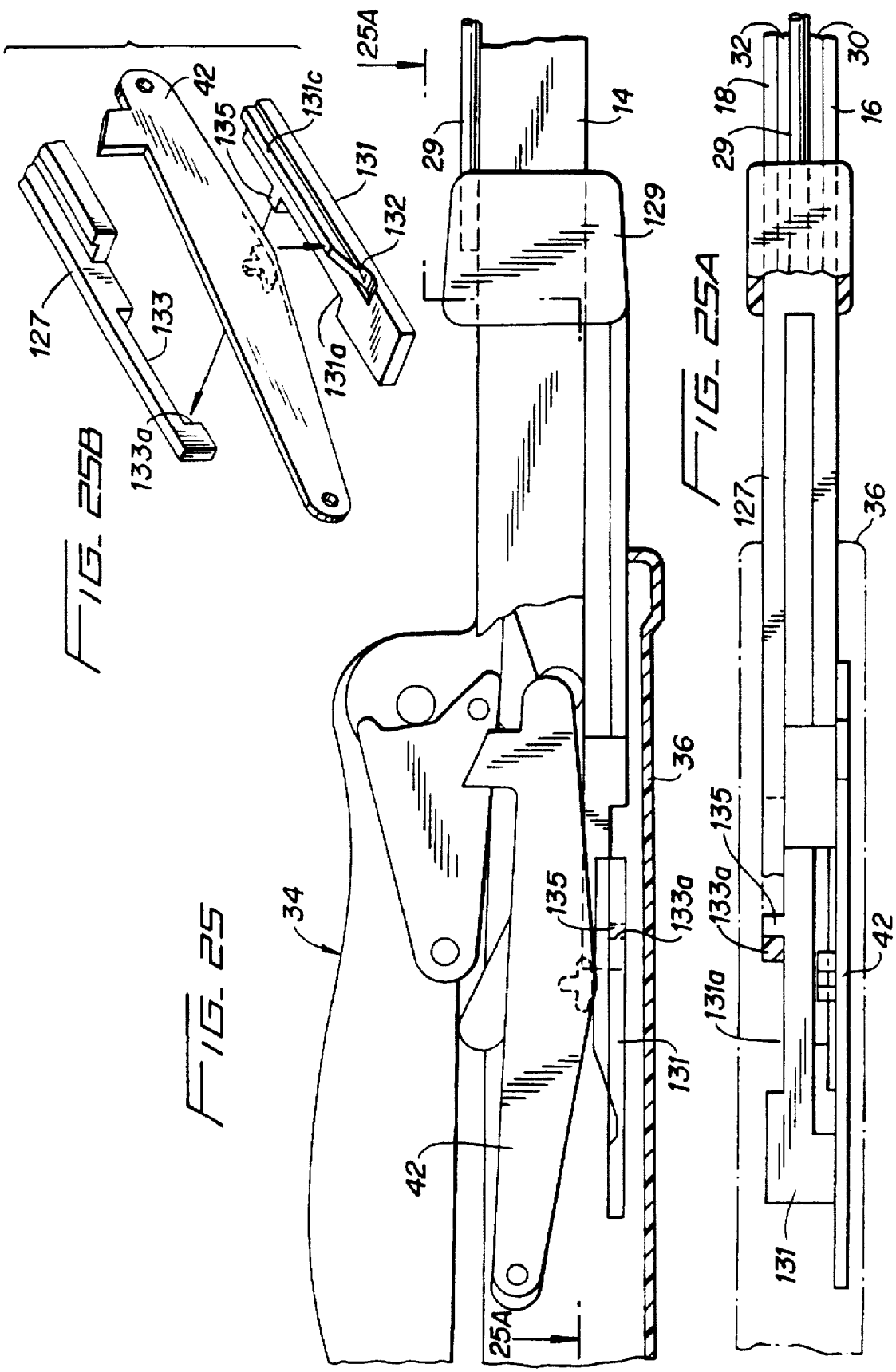

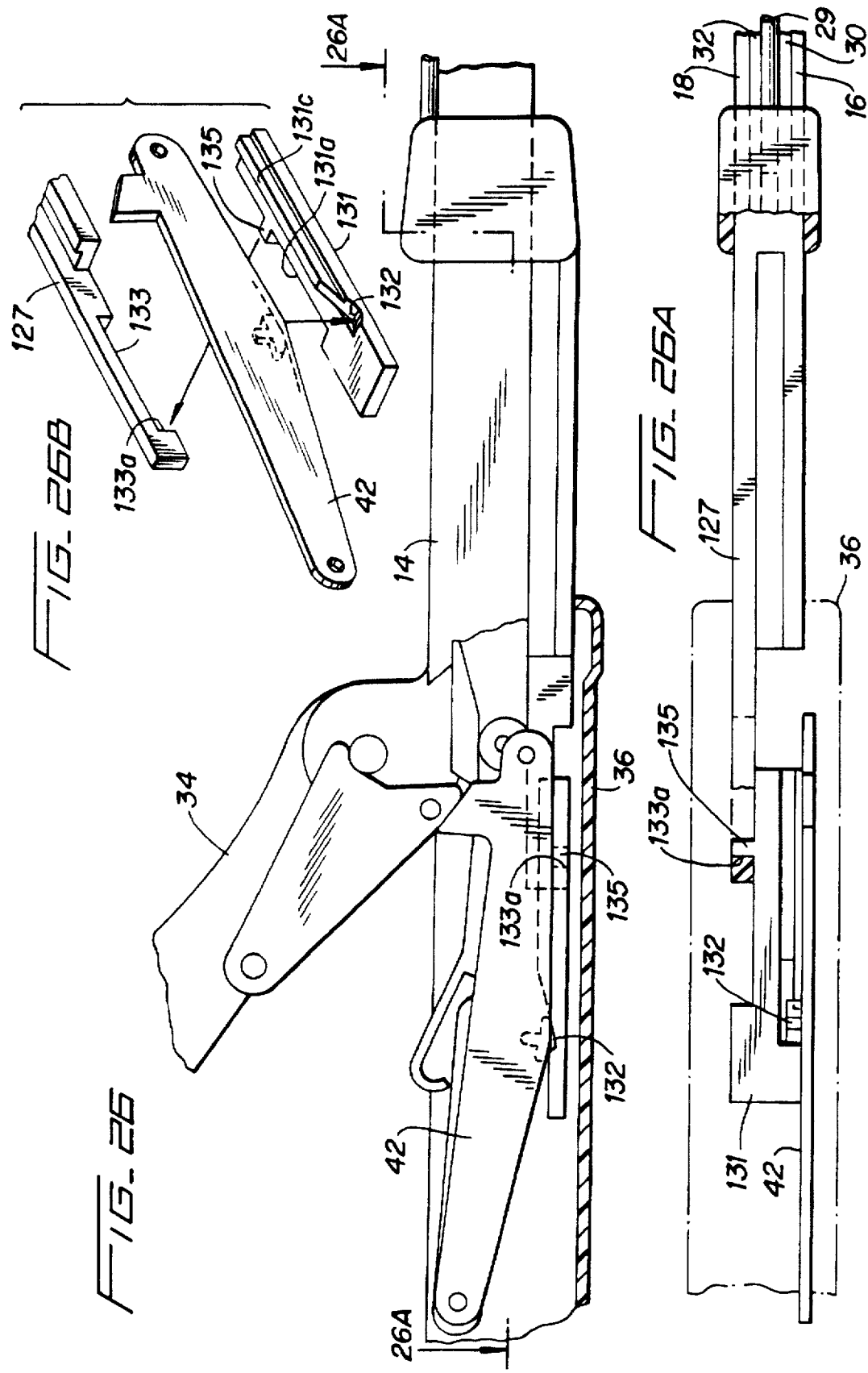

SURGICAL STAPLER WITH ALIGNMENT PIN LOCKING MECHANISM

BACKGROUND OF THE INVENTION

1. Field of the Invention

The present invention relates generally to surgical stapling devices. More particularly, the invention concerns a novel surgical stapler that embodies first and second cooperative, interrelated safety mechanisms that positively prevent the surgeon from refiring the instrument after the staples have been fired, the tissue clamping jaws reopened and the movable jaw guide pin withdrawn.

2. Discussion of the Invention

Surgical staplers are frequently used in surgical procedures for suturing body tissue as, for example, intestinal and gastric walls. Such devices typically include a staple holder, or cartridge, which is disposed on one side of the tissue to be fastened and an anvil assembly on the other side of the tissue. During the surgical procedure, the staples are driven from the cartridge by some type of actuator so that the ends of the staples pass through the tissue and then are bent inwardly by the anvil so as to produce an array of finished fasteners in the tissue. During the typical suturing process, pusher members associated with the cartridge are controllably advanced by the operating mechanism of the instrument in a manner to urge the staples out of the cartridge, through the tissue and forceably against the anvil.

Possibly the most frequently used type of surgical stapler is the linear stapler, which is a device that enables the surgeon to simultaneously place one or more rows of surgical staples in body tissue or organs. By way of example, a typical procedure is a pneumectomy, that is a removal of a portion of a patient's lungs. The linear stapler can be used several times during this procedure, including for the occlusion of the pulmonary artery prior to its resection. For this later use, the surgeon first clamps the jaws of the stapler across the artery, then forms the staples and, prior to reopening the stapler jaws, cuts the artery using the edge of the staple jaws as a guide.

Some prior art linear staplers of conventional design embody a stationary jaw including a staple forming anvil, a movable jaw which carries the staple cartridge and a movable lever which, when initially actuated, causes the stapling cartridge to be moved into an approximated position wherein the cartridge is adjacent to the anvil against which the staples are formed. A retractable guide pin, which typically extends through a guideway in the staple cartridge, guides travel of the movable jaw and staple cartridge and functions to retain the tissue between the jaws during the approximation step. In the approximated position the tissue is captured and compressed between the cartridge and the anvil to a thickness small enough to ensure proper staple formation.

When the operating lever on the handle of the instrument is squeezed a second time, the staples are fired, that is the staples are forcefully urged toward the anvil thereby penetrating the tissues to be stapled and causing the staples to be formed into a "B"-shaped configuration which ensures tissues coaptation and hemostasis. After the staples are formed, the surgeon can, if desired, cut the tissue using the edge of the staple jaws as a guide and then retract the guide pin and reopen the instrument. As the instrument opens, the stapled tissues are freed and the instrument is returned to its original starting configuration. One such prior art linear staple is sold by 3M Health Care of St. Paul, Minn. under the name PI-55".

The environment in the operating room during a surgical procedure can be, at times, complex and confusing, even for experienced operating room staff. For example, after the first staple line has been placed by the surgeon, the stapling instrument is passed back to the scrub nurse, whose job it is to remove and discard the empty cartridge, and replace it with a fresh one, prior to passing it back to the surgeon for another application. If the scrub nurse becomes accidentally distracted, he or she may forget to do so, and might simply pass the instrument containing the empty cartridge back to the surgeon. In prior art surgical staplers, the surgeon can determine that the instrument has been approximated by merely observing the instrument. However, nothing in the appearance of some the prior art instruments indicates that the staples have been fired. Other prior art instruments, such as the "PI-55" offer a visual indicator, but this indicator is located next to the tissues, i.e. in an area where visibility might be limited. If the stapler is misused in this manner, a potentially serious situation can arise since frequently, prior to reopening the instrument, the surgeon cuts the stapled tissues. Should the surgeon erroneously conclude that he has fired the staples when, in fact, he has only approximated the cartridge to the anvil and, therefore, proceed to cut unstapled tissues, a hemorrhage could occur when the surgeon reopens the instrument. This situation is further aggravated by the fact that, as a general rule, the prior art staplers provide so much mechanical advantage to the user that the force needed to be applied on the lever to form the staples is often no greater than the force required to approximate the cartridge to the anvil. Accordingly, the prior art devices fail to provide any tactile feedback that the instrument has, in fact, been fired.

In an application filed by the present inventors on Mar. 7, 1995, two approaches to preventing the surgeon from refiring a spent cartridge are disclosed. U.S. Pat. No. 5,413,267 issued to Solyntjes et al discloses an alternate means for indicating that the staple cartridge contained within the instrument has been fired. However, unlike the apparatus of the present invention, the Solyntjes et al apparatus does not include first and second cooperatively, interrelated safety mechanisms which provide an effective means for indicating to the surgeon that the staple cartridge then in place within the instrument has been fired.

The thrust of the present invention is to provide interrelated locking mechanisms which cooperate to positively indicate to the surgeon that the staples have, in fact, been fired from the cartridge which is in place within the device and to mechanically prevent operation of the staple firing mechanism. As will be better understood from the description that follows, once the staples have been fired, the clamping jaws opened and the guide pin withdrawn, the first and second locking mechanisms cooperate in a highly novel manner to effectively disable the device until a filled staple cartridge is in place within the instrument and the guide pin moved into a fully advanced position relative to the stationary jaw. So long as a fresh staple cartridge is present within the instrument, the device can be used in normal fashion to clamp the tissue and fire the staples, but once the staples have been fired, the instrument is effectively disabled until the spent cartridge is replaced with a fresh, unfired cartridge.

In one embodiment of the invention, the first locking mechanism is carried by the staple cartridge, while in another form of the invention, the mechanism is connected to the movable jaw of the instrument. In either case the first locking mechanism functions to positively prevent complete advancement of the retractable guide pin. Unless and until the guide pin is fully advanced, the first locking mechanism will cooperatively interact with the second backup locking mechanism in a manner to prevent operation of the staple driving mechanism.

SUMMARY OF THE INVENTION

By way of summary, the improved surgical stapler of the present invention comprises a supporting frame, including a stationary jaw having an anvil, a movable jaw, a staple cartridge carried by the movable jaw, means for moving the movable jaw forward the stationary jaw, a retractable guide pin for guiding travel of the movable jaw and operating means for firing the device so as to crimp the staples against the anvil in a manner to enable the surgeon to substantially simultaneously place one or more rows of surgical staples in organs or tissues. In its preferred form, the improved instrument comprises unique first and second cooperatively, interrelated lockout means for positively preventing the staple firing function unless a fresh, unfired staple cartridge is in position within the instrument. The second means functions as a back up to the first lockout means so as to provide a means for indicating to the surgeon that the staple cartridge then present within the device has been fired.

It is an object of the invention to provide a surgical stapler of the character described in the preceding paragraph in which the first lockout means comprises a lockout mechanism that is carried by the staple cartridge itself and functions to prevent advancement of the guide pin to its fully advanced position, once the staples have been fired from the cartridge.

Another object of the invention is to provide a surgical stapler of the type described in the preceding paragraph in which a tactile feedback is provided to the surgeon positively indicating that a spent cartridge, rather than a fresh cartridge is in position within the device.

Another object of the invention is to provide, an alternate form of surgical stapler wherein the first lockout means comprises a part of the movable jaw of the instrument and functions to prevent return of the guide pin to its fully advanced position once the staples have been fired, the jaws have been opened and the guide pin withdrawn from the staple firing orientation.

Another object of the invention is to provide a surgical stapler of the character described in the preceding paragraphs in which the second lockout means of the invention is deployed within the handle portion of the instrument and is operably interconnected with the guide pin for movement between a locked position preventing staple firing and a release position permitting staple firing.

Another object of the invention is to provide a surgical stapler of the character described in the preceding paragraphs in which the jaws of the instrument can be approximated even though actuation of the staple firing operating means is prevented.

Another object of the invention is to provide a device of the character described in which, in one form of the invention, the second lockout means physically engages the operating bar of the operating means to prevent its advancement, and in an alternate embodiment of the invention acts upon the operating linkage of the device in a manner to block approximation of the movable jaw assembly relative to the stationary jaw.

Another object of the invention is to provide a surgical stapler of the class described which can be easily implemented into the prior art linear staplers, is easy to use, and is of a simple construction.

BRIEF DESCRIPTION OF THE DRAWINGS

FIG. 1 is a side-elevational view of one form of the surgical stapler of the present invention partly broken away to show internal construction.

FIG. 2 is a top plan view of the surgical stapler shown in FIG. 1.

FIG. 3 is a cross-sectional view taken along lines 3—3 of FIG. 1.

FIG. 3A is an enlarged, generally perspective view of a portion of the second lockout locking means of the invention for preventing staple firing.

FIG. 4 is an enlarged, fragmentary, side-elevational view of the handle portion of the surgical stapler of FIG. 1 partly broken away to show internal construction.

FIG. 5 is an enlarged top plan view of the handle portion of the surgical stapler of FIG. 1 partly broken away to show internal construction.

FIG. 6 is a cross-sectional view taken along lines 6—6 of FIG. 4.

FIG. 6A is an enlarged, fragmentary generally perspective view showing a portion of the second locking means of the invention.

FIG. 6B is an enlarged, generally perspective view similar to FIG. 6A, but exploded to better show the configuration of the movable members.

FIG. 7 is an enlarged side-elevational view of the forward portion of the surgical stapler showing the guide pin of the device retracted and the staple cartridge removed from the movable jaw assembly.

FIG. 8 is a fragmentary, side-elevational view of the handle portion of the instrument illustrating the manner in which the guide pin is advanced toward the seated position of the guide pin as shown by the phantom lines in FIG. 7.

FIG. 8A is an enlarged fragmentary, cross-sectional view of the portion identified as 8A in FIG. 8.

FIG. 9 is a side-elevational view, similar to FIG. 1 but showing the device in an approximated configuration with the tissue to be stapled clamped between the staple-holding cartridge and the anvil of the device.

FIG. 9A is an enlarged view of the portion identified as 9A in FIG. 9.

FIG. 9B is a cross-sectional view taken along lines 9B—9B of FIG. 9.

FIG. 10 is a side-elevational view, similar to FIG. 9, but showing the device in a staple fired configuration with the staple driving operating bar of the device advanced toward the anvil.

FIG. 11 is a greatly enlarged side-elevational view of the forward portion of the stapling instrument illustrating one form of the first locking means of the invention.

FIG. 12 is a cross-sectional view taken along lines 12—12 of FIG. 11.

FIG. 12A is an enlarged, side-elevational view partly in cross section of the portion identified as 12A—12A in FIG. 11.

FIG. 12B is a cross-sectional view taken along lines 12B—12B of FIG. 12A.

FIG. 12C is a cross-sectional view taken along lines 12C—12C of FIG. 12A.

FIG. 13 is an enlarged, fragmentary, side-elevational view similar to FIG. 11 but showing the position of the component parts of the first locking means following the staple firing step.

FIG. 14 is an enlarged, fragmentary, side-elevational view similar to FIG. 12A but showing the position of the component parts of the first locking means of the invention following withdrawal of the guide pin from its second advanced position shown in FIG. 13.

FIG. 14A is a cross-sectional view taken along lines 14A—14A of FIG. 14.

FIG. 15 is an enlarged, generally perspective, exploded view of the locking mechanism of the first locking means.

FIG. 16 is a greatly enlarged end view of one form of staple cartridge of the present invention which carries a first locking means of an alternate construction from that shown in FIGS. 11 through 15.

FIG. 17 is a side-elevational, cross-sectional view of the portion of the staple cartridge shown in FIG. 16.

FIG. 18 is an enlarged fragmentary end view of the staple cartridge shown in FIG. 16 but illustrating the position of the component parts of the cartridge following staple firing and the movement of the locking element of the locking mechanism into a position wherein advancement of the guide pin is blocked.

FIG. 19 is a side-elevational view of the portion of the cartridge shown in FIG. 18.

FIG. 20 is a greatly enlarged end view of an alternate form of staple cartridge of the invention embodying yet another form of locking means of the invention.

FIG. 21 is a side-elevational, cross-sectional view of the portion of the staple cartridge shown in FIG. 20.

FIG. 22 is a side-elevational view of an alternate form of stapling instrument, partly broken away to show internal construction.

FIG. 22A is an enlarged fragmentary, side-elevational view of a portion of the alternate form of stapling instrument of the invention shown in FIG. 22 illustrating the construction of another form of the second locking means of the invention.

FIG. 22B is a cross-sectional view taken along lines 22B—22B of FIG. 22A.

FIG. 22C is a fragmentary, generally perspective view of guide pin assembly of this latest form of the invention.

FIG. 23 is a side-elevational view similar to FIG. 22 but showing the device in a linkage blocking configuration.

FIG. 23A is an enlarged fragmentary, side-elevational view of a portion of the stapling instrument shown in FIG. 23 further illustrating the locking means in a linkage blocking position blocking movement of the linkage subassembly of the apparatus into an overcenter position.

FIG. 24 is a side-elevational view showing still another embodiment of the second locking means of the invention.

FIG. 24A is an enlarged fragmentary view of the handle portion of the embodiment illustrated on FIG. 24.

FIG. 24B is a greatly enlarged, generally perspective view of certain cooperating components of the guide pin and the second locking means of the embodiment shown in FIG. 24.

FIG. 24C is a cross-sectional view taken along lines 24C—24C.

FIG. 24D is a greatly enlarged, generally perspective view of the cooperating linkage and linkage blocking components shown in FIG. 24.

FIG. 25 is a side-elevational view similar to FIG. 24A but showing the guide pin partially advanced toward its second forward-most position.

FIG. 25A is a cross-sectional view taken along lines 25A—25A of FIG. 25.

FIG. 25B is a generally perspective view similar to FIG. 24D but showing more clearly the relationship of the cooperating linkage and linkage blocking components shown in FIG. 25.

FIG. 26 is an enlarged side-elevational view similar to FIG. 25 but showing the guide pin fully advanced into its second most forward position.

FIG. 26A is a cross-sectional view taken along lines 26A—26A of FIG. 26.

FIG. 26B is a generally perspective view similar to FIG. 25B showing more clearly the relationship of the cooperating linkage and linkage blocking components shown in FIG. 26.

DESCRIPTION OF THE INVENTION

Referring to the drawings and particularly to FIGS. 1 through 3, one form of the apparatus of the invention for simultaneously emplacing a plurality of surgical staples into tissues and organs is there shown and generally designated by the numeral 12. The apparatus comprises an elongated supporting frame 14 having first and second longitudinally extending spaced walls 16 and 18 defining an interior space 20 (FIG. 3). Forming an integral part of frame 14 is a stationary jaw assembly 21 which includes an anvil portion 22 having a staple-engaging face 24.

Slidably movable within frame 14 from a first retracted position to a second forward position is a movable jaw assembly 26. Removably deployed within movable jaw assembly 26 is a staple cartridge 27 (FIG. 7) which contains a plurality of surgical staplers that are adapted to pass through the tissue to be stapled and then crimped against face 24 of anvil 22 in a manner presently to be described.

As indicated in FIG. 7, a pusher member 28 is associated with cartridge 27 for movement relative to the cartridge housing 27a between a first extended position as shown in FIGS. 7 and 9 to a second stapled fired position shown in FIG. 10. During the firing step, pusher member 28 engages the staples contained within the staple cartridge and drives them forwardly into pressural engagement with face 24 of anvil portion 22. As the staples are simultaneously driven from the staple cartridge, they will engage the anvil face and typically crimp into a crimped shaped roughly corresponding to the shape of the letter "B". As the staples are appropriately crimped, they will, of course, join together the layers of tissue or organ "T" between face 24 of the anvil and the forward face of the staple cartridge.

In operating the instrument, when the staple cartridge, along with its cooperating pusher member, is disposed in the spaced-apart relationship with anvil 22 as shown in FIG. 7, tissue or human organ can be placed in the open space between the staple cartridge and face 24 of the anvil. After the tissue has been appropriately positioned between the staple cartridge and the anvil, guide means, which here includes an elongated retractable guide pin 29, is moved forwardly to the second advanced position shown by the phantom lines in FIG. 7. Next, using the approximation means of the invention, movable jaw assembly 26 along with staple cartridge 27, is moved forwardly of the apparatus to a location where it is closely adjacent face 24 of anvil 22 (see FIG. 9). During travel of jaw assembly 26 and staple cartridge 27, guide pin 29 maintains proper alignment of the components and also functions to retain the tissue "T" in position between jaw assemblies 21 and 26.

As can best be seen by referring to FIGS. 1, 2, and 3, movable jaw assembly 26 includes a pair of spaced-apart approximation members 30 and 32, the forward portions of which define the cartridge receiving portion 26a (FIG. 2). Members 30 and 32 are disposed between side walls 16 and 18 and, in a manner presently to be described, are slidably movable with respect thereto from a first retracted position shown in FIGS. 2 and 7 to a forward, approximated position shown in FIG. 9.

In the embodiment of the invention shown in FIG. 1 through 10, the means for moving the movable jaw assembly toward the stationary jaw includes a handle assembly 34 which comprises a fixed handle portion 36 and a movable handle portion, or actuating lever 37, which is pivotally connected to fixed handle portion 36 in the manner best seen in FIGS. 1 and 4. Additionally, these approximation means further include an operating linkage 34a made up of pivotally interconnected first and second operating links 38 and 40 (FIG. 4). The first end 38a of link 38 is pivotally interconnected both with frame 14 and with a third link member 42 by a pivot pin 39. The second end 38b of link 38 is pivotally connected to link 40 proximate its first end 40a by a pivot pin 39a. The second end 40b of link 40 is operably associated with members 30 and 32 and moves these members forwardly as the linkage is moved into the collapsed, overcenter configuration shown in FIGS. 9 and 10. With this construction, when actuating lever 37 is moved from the first position shown in FIG. 1 to the second position shown in phantom lines in FIG. 9, linkage assembly 34a will be moved by lever 37 from the extended position shown in FIG. 1 to the collapsed position shown in FIG. 9. As linkage 34a moves into this collapsed, overcenter position, members 30 and 32 are urged forwardly to the position shown in FIG. 9. A first biasing means, shown here as an elongated coil spring 45, (FIG. 4) yieldably resists depression of lever 37. Similarly, a second biasing means, here provided as a torsion spring 46, yieldably resists movement of linkage assembly 34a from the upraised position shown in FIG. 1 to the collapsed or closed position shown in FIG. 9. As will be discussed in the paragraphs which follow, spring 46 tends to automatically return linkage 34a to the upraised position when it is moved by a novel release means from the downward, overcenter position shown in FIG. 9 toward the open, upstanding position shown in FIG. 1.

It is to be noted that movement of the generally "T" shaped members 30 and 32, which are slidably received within spaced-apart walls 16 and 18 of frame 14, is yieldably resisted by a third biasing means which comprises an elongated coil spring 47 having an end 47a connected to the supporting frame and an end 47b connected to the members 30 and 32 (FIG. 4).

Formed proximate the forward end of members 30 and 32 is the previously identified movable jaw assembly 26 which removably receives staple cartridge 27. With this construction, it is apparent that the forward movement of members 30 and 32 caused by the initial closing of lever 37 will result in the staple cartridge moving into the approximated position wherein it is located adjacent anvil 22 (FIG. 9). The device will remain in this approximated position until it is released by the release means of the invention in a manner presently to be described.

Following the approximation step, the staples can be driven through the tissue "T" and into pressural engagement with the anvil 22 by the operating means of the invention. In the form of the invention shown in the drawings, the operating means comprises a generally "T" shaped operating bar 56 which is slidably movable between members 30 and 32 from a first retracted position shown in FIGS. 2 and 9 to a second staple fired position shown in FIG. 10. The operating means also comprises an operating member or link 52 which is pivotally connected to handle portion 37 for pivotal movement between first and second positions. As best seen in FIG. 10, operating link 52 includes an end portion 52a which is movable into engagement with operating bar 56 following movement of lever 37 to its third retracted position shown by the phantom lines in FIG. 10.

As can be observed by also referring to FIG. 1, prior to the approximation step, operating link 52 is maintained in its first upraised position by the rearwardly positioned members 30 and 32. However, upon movement of these members forwardly of the apparatus into the approximated position shown in FIG. 9, and upon movement of handle portion 37 from its second downward position shown by the phantom lines in FIG. 9 to its third upward position shown by the phantom lines in FIG. 10, member 52 will pivot downwardly due to the urging of a fourth biasing means shown here as a torsion spring 56 (FIG. 4). With member 52 in this downward position, movement of handle 37 into the fourth downward position shown by the solid lines in FIG. 10 will cause end 52a of member 52 to engage the T-shaped bar 56 and cause it to move forwardly between member 30 and 32 from the position shown in FIG. 9 to the forward staple fired position shown in FIG. 10. As the T-shaped bar moves forwardly toward staple cartridge 27, it will engage the pusher members and force the staples from the cartridge through the tissue to be coapted and into pressural engagement with anvil 22. In the prior art staplers, spring 45 would then tend to urge lever 28 into its normal upraised position. Visual observation of the device after firing would, therefore, require that the surgeon both remember to, and have the opportunity to, observe whether carriage pusher members 28 have disappeared from the field of view created by a hole XX (FIG. 10). If the pusher members are not visible, the surgeon could conclude that the cartridge had been fired. On the other hand, if the pusher members are still visible, the surgeon could conclude that the cartridge has not yet been fired. While this is better than no feedback at all, it is not ideally suited for the busy environment of the operating room nor to the lack of visibility associated with many procedures in which the stapler is used.

After the staples have been fired, the release means of the device is used to return the linkage assembly to its starting position. The release means shown in FIGS. 1 through 10 comprises a manually operated release pin assembly 66 which is movable within a slot 67 formed in the handle portion of the apparatus from a first downward position to a second upward release position (FIGS. 5 and 9). The release pin assembly 66 here includes a knob portion 68 which is interconnected with a shaft portion 70 that extends through and is guided by slot 67. The inboard end of shaft 70 is interconnected with linkage assembly 34a so that an upward movement exerted on knob 68 will move the linkage assembly from the downward, overcenter position shown in FIG. 9 toward the upward, starting position shown in FIG. 1. As knob 68 is moved upwardly, the linkage assembly will rapidly snap into the upward starting position as a result of the action of torsion spring 46.

Forming an important aspect of the present invention is the provision of cooperating, interrelated first and second locking means which function to effectively disable the instrument unless a fresh staple cartridge is in position within the movable jaw of the device. In the present form of the invention, the first lockout locking means functions to engage guide pin 28 in a manner to positively prevent its advancement toward the second advanced position shown by the phantom lines of FIG. 7 wherein it is seated within bore 21a provided in stationary jaw 21. In a manner presently to be described, this first locking means uniquely cooperates with the second lockout locking means to prevent a staple firing advancement of operating bar 56 unless a fresh staple cartridge is in place within the instrument and the guide pin is fully advanced into its second advanced position. This unique backup feature provides a clear and unmistakable signal to the surgeon as to the condition of the cartridge that is in place within the instrument.

Turning to FIGS. 11 through 15 one form of the first locking means of the invention is there illustrated. This first locking means here comprises a novel locking mechanism 75 of the character best seen in FIGS. 11 and 15. Mechanism 75 is carried by movable jaw 26 and comprises a uniquely channeled platform 76 which is connected to movable jaw 26. Carried by platform 76 is a first member 78, which includes a generally triangularly shaped pusher engaging extremity 80, and a second cooperating member 82 (FIG. 5). Member 82 includes a yoke-like locking extremity 82a which, in a manner presently to be described, is receivable within a guideway 84 formed in pin 29 and is movable therewithin into locking engagement with longitudinally spaced apart locking shoulders formed at the opposite ends of the guideway (FIG. 14). As best seen in FIGS. 14 and 14a, guideway 84 is formed by milling or otherwise forming the opposing sides of pin 29 in a manner to provide longitudinally extending, generally flat surfaces which define the guideway. Formed at one extremity of the guideway 84 is a shoulder 85 and formed at the opposite end thereof is a shoulder 86 (FIG. 14).

Also comprising a part of the locking mechanism of this form of the invention is a biasing means for urging first member 78 outwardly of platform 76 and into engagement with pusher members 28a in the manner shown in FIG. 11. The biasing means also functions to simultaneously urge second locking member 82 upwardly into engagement with guide pin 29 in the manner shown in FIG. 11. In the embodiment of the invention shown in the drawings, the biasing means is provided in the form of a clip-type spring 89, the configuration of which is best seen by referring to FIG. 15. When spring 89 is in position within block 76, leg 89a of the spring engages the inboard end 78a of member 78 and urges the member outwardly of the housing in a direction toward the pusher members 28. In similar fashion, leg 89b of spring 89 engages the inboard end 82b of member 82 and tends to urge the member upwardly into pressural engagement with guide pin 29. Member 78 is provided with a generally V-shaped cutout portion 78c which lockably engages a fulcrum-like member 82c provided on member 82 when member 78 is moved by spring 89 into the extended position best seen in FIG. 14.

Turning once again to FIG. 11, it can be observed that with the movable jaw in the approximated position and with pusher members 28 extending rearwardly from the fresh staple cartridge 27 that is deployed within the movable jaw, forward movement of locking member 78, due to the urging of spring 89, will be prevented by the rearwardly extending pusher members 28. Similarly, in this configuration, the second locking pin 82 will be retained in its retracted position within block 76 by the fulcrum-like protuberance 82c of member 82 engaging member 78 in the manner shown in FIGS. 11 and 12A. However, upon operating bar 56 moving forwardly in a manner shown in FIG. 13 to urge pusher members 26 into firing engagement with the staples disposed within staple cartridge 27, the pusher members will no longer impede forward movement of locking member 78. Accordingly, leg 89a of spring 89 will urge member 78 forwardly of the platform 76 in the direction of the arrow in FIG. 13. As member 78 moves forwardly, or to the right as viewed in FIG. 13, V-shaped slot 76c will move into register with the fulcrum-like protuberance 82a provided on member 82 thereby causing spring leg 84b to urge member 82 upwardly into the position shown in FIG. 13 wherein yoke-shaped end portion 82a engages the outer cylindrical surface of guide pin 29. Following the staple firing step and during the subsequent retraction of guide pin 29, the yoke-shaped extremity 82a of member 82 will move into the guideway 84 formed on pin 29 and then into engagement with shoulder 85 in the manner shown in FIG. 14.

If the surgeon attempts to advance the guide pin without replacing the spent cartridge, extremity 82a of locking pin 82 will move into engagement with shoulder 86 thereby blocking further advancement of the guide pin and providing a tactile sensation to the surgeon. In this regard, it is to be noted that the length of guideway 84 is such that the guide pin cannot be fully advanced to its forward most second position so long as locking pin 82 is in the extended position. Thus the tactile indication given to the surgeon as pin 82 engages shoulder 86 advises the surgeon that forward travel of the pin is blocked thereby providing a positive input that a spent cartridge is in place within the instrument.

Upon insertion of a fresh cartridge into the movable jaw assembly of the instrument, the extended pusher members of the fresh cartridge will move locking pin 78 to the left as viewed in FIG. 14 against the urging of leg 89a of spring 89. This rearward movement of member 78 will also cause member 82 to be cammed downwardly against the urging of leg 89b of spring 89 so that the locking mechanism will be returned to the starting configuration shown in FIGS. 11 and 12A. With the component parts in this position and with blocking member 82 in its retracted location, it is apparent that guide pin 29 can be freely moved forwardly of the device and into its fully advanced second position. This freedom of movement of guide pin 29 into its fully advanced second position indicates to the surgeon that a fresh cartridge is in place within the instrument and that use of the instrument can safely proceed.

Referring particularly to FIGS. 1, 3A, and 6, one form of the second locking means of the invention is there illustrated and can be seen to comprise a locking gate 90 which is carried by handle portion 36 for movement between a first locking position shown in FIG. 6 and a second release position shown in FIG. 9B. In the present form of the invention, the release means comprises an elongated release segment or member 92 which is slidably receivable within a central aperture 90a formed in locking gate 90 (FIG. 3A). Member 92 includes a camming extremity 92a for engagement with gate 90 to move the gate into the second release position shown in FIGS. 9 and 9A upon movement of guide pin 29 into its second forward most advanced position shown in FIG. 9 wherein the forward extremity of the guide pin is received within bore 21a formed in stationary jaw 21.

As best seen by referring to FIGS. 3A, 8 and 9, release segment 92 as well as pin 29 are connected to a slide member 94 which is slidably movable relative to frame 14 in the manner shown by the arrow in FIG. 8. With this construction, when slide member 94 is in its rearward most position adjacent handle portion 36 release segment 92 fully extends into handle 36 (FIG. 1). However, as slide member 94 is moved forwardly in the manner indicated in FIG. 8, segment 92 will be withdrawn from handle portion 36 in a manner such that the camming segment 92 moves forwardly in a direction toward locking gate 90. When slide member 94 is moved to its furthermost forward position (as shown in FIG. 9), segment 92 will be substantially entirely withdrawn from handle 36 and camming extremity 92a will move into engagement with locking gate 92 so as to urge it downwardly into a recess 36a formed proximate the forward end of handle portion 36 in the direction of the arrow shown in FIG. 9A.

It is to be understood that when the elongated release segment 92 is in this forward most position, guide pin 29 is also in its forward most position with the forward extremity of the pin extending into bore 21a of fixed jaw 21. When, and only when, the components are in the position indicated in FIG. 9, will the operating bar 56 be free to move into engagement with pusher members 28 in a manner to urge them into driving engagement with the staples contained within staple cartridge 27.

Referring particularly to FIGS. 6, 6A, 6B, 9 and 9A, it is to be observed that, operating or T-bar member 56, is provided with an elongated slot 96 within which gate 90 can travel. Slot 96 terminates at its forward end in a shoulder 96a and in its rearward end in a shoulder 96b. Prior to gate 94 being cammed downwardly into the release position shown in FIG. 9A, forward movement of the T-bar 56 is limited by gate 90 moving into blocking engagement with locking surface or shoulder 96b. Only after the locking gate has been moved into its release position by camming extremity 92a moving into the position shown in FIGS. 9 and 9A will further forward travel of operating bar 56 be possible. Consequently, with this novel construction, it is readily apparent that unless and until guide pin 29 is advanced fully into its second position, locking gate 90 will limit the forward travel of the operating member 56 and prevent its advancement into the staple firing position shown in FIG. 10.

So long as a spent cartridge is deployed within the instrument, the first locking means of the invention will prevent advancement of guide pin 29 into its second, forward most position. When this is the case, the second locking means, which includes gate 90, will positively prevent advancement of operating bar 56 into the staple firing configuration. This cooperative interaction between the first and second locking means of the invention provides an indication to the surgeon that a spent cartridge is deployed within the instrument and that the spent cartridge must be replaced with a fresh cartridge before proceeding with its use.

It is to be observed that, although locking gate 90 effectively prevents movement of operating bar 56 into the staple firing position shown in FIG. 10, the novel design of the second locking means (see FIGS. 6, 6A and 6B) does not prevent forward movement of members 30 and 32. More particularly, as shown in FIGS. 6, 6A and 6B, members 30 and 32 are provided with elongated slots 30a and 32a which permit advancement of these members past gate 90 into a forward approximated position. Accordingly, the jaws of the instrument can be approximated even though guide pin 29 is not in its forward most position. However, for the reasons discussed in the preceding paragraphs, the surgeon is positively prevented from moving the actuating T-bar 56 forwardly to the position shown in FIG. 9. Only when pin 29 is fully seated thereby permitting release segments 92 to cam gate 90 downwardly in the manner shown in FIG. 9A, will the surgeon be able to advance the operating T-bar 56 into the staple driving configuration shown in FIG. 10.

Turning next to FIGS. 16 through 19, an alternate form of the first locking means of the invention is there illustrated. In this embodiment of the invention, the second locking means comprises a novel guide pin interference means for blocking the advancement of the guide pin. This means is here provided as a novel mechanism 100 which forms a part of a modified staple cartridge assembly 102 having a body portion 102a which is provided with a pin receiving bore 102b. Mechanism 100 includes a pin interference member 104 having a cover portion 104a an integrally formed leg-like locking portion, or member 104b. Member 104 is movable from the first retracted position shown in FIG. 16 to the second pin interfering position shown in FIG. 18 wherein cover portion 104 covers the pin receiving bore 102b. Also forming a part of the interference mechanism of this form of the invention is a biasing means for continuously urging interference member 104 toward the second interfering position shown in FIG. 18. The biasing means is here provided in the form of a generally U-shaped spring 108, a first leg 108a of which is connected to staple cartridge 102 and a second leg 108b of which is connected to member 104 in the manner shown in FIG. 16.

With the apparatus in the configuration shown in FIG. 16, leg 104b engages an edge 28a formed on the outwardly protruding pusher member 28 (see also FIG. 17). Referring to FIGS. 18 and 19, it is to be observed that, during the staple firing step in which the pusher member 28 is moved inwardly of cartridge 102, edge 28a of the pusher member will move inwardly out of the way of locking segment 104b thereby permitting spring 108 to move the interference member from the first position shown in FIG. 16 to the second interfering position shown in FIG. 18. In this pin interfering position, advancement of the guide pin, which is shown in FIG. 19 by the phantom lines, will be blocked by cover portion 104a of the interference member thereby preventing the guide pin from entering bore 102b and advancing into its second forward most position in engagement with stationary jaw 21.

When the alternate form of first locking means of the invention is used in connection with an instrument which embodies the previously described, second locking means of the invention, the inability of the surgeon to advance guide pin 29 into its forward most second position will also prevent the full advancement of release segment 92 of the second locking means. Accordingly, locking gate 90 will remain in an upraised locking position blocking forward movement of operating T-bar 56 into a staple firing configuration. Once again, this cooperative interaction between the first and second locking means of the invention effectively disables the instrument unless and until a fresh staple cartridge is deployed within the device so that the guide pin 29 can be advanced by the surgeon into its second fully advanced position.

Turning to FIGS. 20 and 21 still another form of the first locking means of the invention is there illustrated. This locking means is similar in many respect to the form shown in FIGS. 16 through 19 and like numerals are used to identify like components. In this embodiment of the invention, the first locking means also comprises a novel guide pin interference means for blocking the advancement of the guide pin. This means, like the means shown in FIGS. 16 through 19 comprises mechanism 100 which forms a part of an alternate type of modified staple cartridge assembly 111 having a body portion 111a which is provided with a guide pin receiving bore 111b.

Modified staple cartridge 111 is of a character adapted for use with a surgical stapler in which the pusher members that engage the staples form a part of the operating assembly of the instrument rather than a part of the staple cartridge. As before, mechanism 100 includes a guide pin interference member 104 having a cover portion 104a an integrally formed leg-like locking portion, or member 104b. Member 104 is movable from the first retracted position shown in the solid lines of FIG. 20 to the second, pin interfering position shown in the phantom lines of FIG. 20 wherein cover portion 104a covers the pin receiving bore 111b. Also forming a part of the interference mechanism of this form of the invention is a biasing for continuously urging interference member 104 toward the second interfering position shown in the phantom lines in FIG. 20. The biasing means is here provided in the form of a generally U-shaped spring 108, a first leg 108a of which is connected to staple cartridge 111 and a second leg 108b of which is connected to member 104 in the manner shown in FIG. 20.

With the apparatus in the configuration shown in the solid lines of FIG. 20, leg 104b engages an edge 113a formed on an outwardly protruding locking pin or member 113 which is telescopically receivable into a second bore 114 formed in body portion 111a. During the staple firing step in which the operating bar is advanced, the pusher assembly that is connected to the operating bar is moved inwardly of cartridge 111. As the pusher assembly moves inwardly, it will contact member 113 causing it to move inwardly out of the way of locking segment 104b in the manner shown by the arrow and the phantom lines of FIG. 21. with member 113 out of the way, spring 108 will move the interference member 104 from the first position shown by the solid lines in FIG. 20 to the second interfering position shown by the phantom lines in FIG. 20. In this guide pin interfering position, advancement of the guide pin, which is shown in FIG. 21 by the phantom lines, will be blocked by cover portion 104a of the interference member thereby preventing the guide pin from entering bore 111b and advancing into its second forward most position in engagement with stationary jaw 21.

When this latest form of first locking means of the invention is used in connection with an instrument which embodies the previously described, second locking means of the invention, the inability of the surgeon to advance guide pin 29 into its forward most second position will also prevent the full advancement of release segment 92 of the second locking means. Accordingly, locking gate 90 will remain in an upraised locking position (see FIG. 6) blocking forward movement of operating T-bar 56 into a staple firing configuration. As before, this cooperative interaction between the first and second locking means of the invention effectively disables the instrument unless and until a fresh staple cartridge is deployed within the device so that the guide pin 29 can be advanced by the surgeon into its second fully advanced position.

Referring next to FIGS. 22, 22A, 22B, 22C, 23, and 23A, an alternate form of the second locking means of the invention is there illustrated. This form of second locking means is somewhat similar to that shown in FIGS. 1 through 10 and like numbers are used to identify like components. This second locking means uniquely functions to selectively disable the operating linkage of the apparatus and here comprises a guide pin assembly which, as shown in FIG. 22C, is similar in many respects to that shown in FIG. 3A. However, this modified assembly includes an elongated linkage blocking means or segment 122 which is connected to a slide member 124 and is slidably receivable within handle portion 36. Segment 122 includes a blocking extremity 122a for blocking engagement with linkage 34a. More particularly, following staple firing and upon movement of guide pin 29 into the first retracted position shown in FIG. 23, blocking extremity 122a moves to a location below linkage assembly 34a preventing movement thereof into the overcenter, locked position shown in FIG. 22.

Referring particularly to FIGS. 22, 22A and 22C, it can be seen that linkage blocking segment 122 as well as pin 29 are connected to a slide member 124 which, as before, is slidably movable relative to frame 14 from a forward guide pin advanced position to the guide pin retracted position shown in FIG. 22. As indicated in FIGS. 23 and 23A, when slide member 124 is moved into its rearward most position linkage blocking segment 122 extends into handle 36 and extremity 122A engages the linkage assembly and, with the aid of spring 46 (FIG. 4), will urge the assembly into its upwardly extending starting position. this being the case, the release means or release assembly 66 present in the earlier described embodiments is not here required.

So long as segment 122 is in the rearmost position shown in FIG. 23, linkage assembly 34a cannot be moved in the overcenter, locked position. However, if slide member 124 is moved forwardly to its fully advanced position, wherein guide pin 29 engages stationary jaw 21, segment 122 will be withdrawn from handle portion 36 in a manner such that extremity 122a clears the linkage assembly and no longer blocks downward movement of the assembly into the overcenter locking position thereby permitting approximation of jaws 21 and 26. However, if the first locking means of the invention, as for example that shown in FIGS. 11 through 15, prevents movement of guide pin 29 to its fully advanced second position, segment 122 will block normal downward movement of the linkage assembly so that the instrument can neither be locked in the approximated position nor fired. Stated another way, when, and only when, the components are in the position indicated in FIG. 22, can the instrument be locked in the approximated position and, upon the subsequent operation of the handle assembly, will the operating bar 56 be free to move into engagement with pusher members 28 in a manner to urge them into driving engagement with the staples contained within staple cartridge 27.

Turning now to FIGS. 24 through 26, still another form of the second locking means of the invention is there illustrated. This form of second locking means is somewhat similar to that just described and like numbers are used to identify like components. This latest form of second locking means also functions to selectively disable the operating linkage 34a of the apparatus and here comprises a guide pin assembly which is similar to that shown in FIG. 22C. However, this assembly includes not only an elongated, rearwardly extending segment 127, which is connected to a slide member 129, but also includes a novel shuttle member 131. (See also FIGS. 24B and 24D) In this latest form of the invention, it is this shuttle member that is selectively movable into blocking engagement with linkage 34a. More particularly, following staple firing and upon movement of guide pin 29 into the first retracted position shown in FIG. 24, segment 127 engages and slidably moves shuttle member 131 to the location shown in FIG. 24 where it is directly below linkage assembly 34a thereby preventing movement of the assembly into the overcenter locked position shown in FIG. 26.

Referring particularly to FIGS. 24A and 24B, it is to be noted that segment 127 as well as pin 29 are connected to a slide member 129 which, as before, is slidably movable relative to frame 14 from a forward guide pin advanced position shown in FIG. 26 to the guide pin retracted position shown in FIG. 24. When slide member 129 is moved into its rearward most position closely adjacent to handle portion 36, (FIG. 24A) segment 127 extends into handle 36 to its maximum extent and urges shuttle 131 to its rearward most, first position shown in FIG. 24A. However, because of the cooperative interaction between segment 127 an shuttle 131, when the slide member 129, along with guide pin 29, is moved to the forward most second position shown in FIGS. 26 and 26A. shuttle 131 is moved forwardly by segment 127 to the non-interfering second position shown in FIG. 26 wherein the linkage can move into a recess 132 formed in the shuttle. In this regard it is to be noted that segment 127 includes an elongated dwell slot 133 (FIG. 24B) within which an engagement pin 135 provided on shuttle 131 is slidably received. With this construction, when, and only when, guide pin 29 is in its forward most position will the end wall 133a of slot 133 engage engagement pin 135 and urge the shuttle forwardly to the position shown in FIG. 26. It should be noted that this feature allows the surgeon who has completed the firing-reopening-pin withdrawal cycle to use the stapler as a clamp. In this form, the instrument could function as an additional clamp, spring-biased in the open position, unless the surgeon squeezes the lever against the handle.

As best seen in FIG. 25, as guide pin 29 is initially advanced a partial distance toward stationary jaw 21, shoulder 133a moves along a slot 131a formed in shuttle 131. However, in this position the shuttle itself remains in a stationary linkage blocking position so that an upstanding shoulder 131c formed on the shuttle prevents movement of linkage 34a into the overcenter position. Only after end wall 133a engages pin 135 will shuttle 131 start to move forwardly to the position shown in FIG. 26 so that the linkage assembly can move into an overcenter position.

It is apparent that when this latest form of second locking means is used with one of the first locking means previously described herein, such, as for example, that shown in FIGS. 11 through 15, the existence of a spent cartridge in the instrument will once again prevent full advancement of the guide pin which, in turn, will prevent movement of shuttle 131 into the non-interfering position shown on FIG. 26. Therefore, until the spent staple cartridge is replaced with a fresh cartridge, the instrument will remain inoperable. Similarly, after the instrument is fired and the guide pin retracted to remove the stapled tissue, shuttle 131 will block complete downward movement of the linkage assembly. To render the instrument operable, the spent staple cartridge must be replaced with a fresh cartridge to enable complete forward movement of the guide pin and advancement of the shuttle into a non-interfering forward position.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. An apparatus for applying surgical staples comprising:
a frame including a stationary jaw;
a movable jaw supported on the frame, the movable jaw being movable into approximation with the stationary jaw;
a cartridge containing a plurality of staples supported on one of the stationary jaw and the movable jaw and an anvil supported on the other of the stationary jaw and the movable jaw;
a guide member movably supported on the frame, the guide member movable from a retracted position to an advanced position to maintain the relative alignment of the stationary jaw and the movable jaw;
a first locking mechanism operatively associated with the guide member, the first locking mechanism being movable to a position preventing movement of the guide member to the advanced position;
an operating member supported within the apparatus, the operating member being movable from a proximal position to a distal position to effect ejection of the plurality of staples; and
a second locking mechanism operatively associated with the operating member, the second locking mechanism being movable from a first position to a second position to prevent movement of the operating member from the proximal position to the distal position.

2. An apparatus according to claim 1, wherein the first locking mechanism is supported on the movable jaw.

3. An apparatus according to claim 1, wherein the guide member includes an elongated pin having a guideway formed therein, the first locking mechanism being movable into the guideway to prevent movement of the elongated pin to the advanced position.

4. An apparatus according to claim 3, wherein the first locking mechanism includes a platform having a channel formed therein and a first member movably positioned within the channel from an unlocked position to a locked position, wherein in the locked position, the first locking mechanism extends into the guideway.

5. An apparatus according to claim 4, wherein the first locking mechanism further includes a cooperating member movably positioned within the channel, the cooperating member being operatively associated with the first member such that when the first member is in the unlocked position, the cooperating member is spaced from the guide member, and when the first member is in the locked position, the cooperating member extends into the guideway.

6. An apparatus according to claim 4, further including at least one pusher member operatively associated with the operating member, the pusher member being movable from a loaded position to a fired position to effect ejection of the plurality of staples.

7. An apparatus according to claim 6, wherein when the pusher member is in the loaded position, the pusher member engages the first member of the first locking mechanism to retain the first member in the unlocked position.

8. An apparatus according to claim 7, wherein the first locking member further includes a biasing member positioned within the channel, the biasing member being positioned to bias the first member to the locked position, wherein when the pusher member is moved to the fired position, the first member is biased to the locked position by the biasing member.

9. An apparatus according to claim 1, wherein the cartridge is removable and the first locking mechanism is supported on the removable cartridge.

10. An apparatus according to claim 9, wherein the cartridge includes a guide bore, the guide member being movable through the guide bore during approximation of the movable jaw and the stationary jaw.

11. An apparatus according to claim 10, wherein the first locking mechanism includes an interference member, the interference member being movable from a first position permitting passage of the guide member through the guide bore to a second position blocking passage of the guide member through the guide bore.

12. An apparatus according to claim 11, further including a biasing member, the biasing member urging the interference member to the second position.

13. An apparatus according to claim 12, further including at least one pusher member operatively associated with the operating member, the at least one pusher member being movable from a loaded position to a fired position in response to movement of the operating member from the proximal position to the distal position to effect ejection of the plurality of staples.

14. An apparatus according to claim 13, wherein when the at least one pusher member is in the loaded position, the at least one pusher member operatively engages the interference member to retain the interference member in the first position.

15. An apparatus according to claim 1, wherein the frame includes a handle portion, the second locking mechanism being at least partially positioned within the handle portion.

16. An apparatus according to claim 15, wherein the second locking mechanism includes a locking gate, the locking gate being movable between a first locking position to block movement of the operating bar and a second release position permitting the operating member to move to the distal position.

17. An apparatus according to claim 16, further including a release member having a cam surface, the cam surface being movable into engagement with the locking gate to move the locking gate to the release position.

18. An apparatus according to claim 17, wherein the release member is fastened to the guide member and is movable therewith, the cam surface engaging the locking gate after the stationary jaw and the movable jaw have been approximated a predetermined amount.

19. An apparatus according to claim 15, further including a movable handle assembly having a linkage operatively connected to the operating member and an actuating lever operatively connected to the linkage.

20. An apparatus according to claim 19, wherein the second locking mechanism includes a blocking member, the blocking member in the second position substantially preventing movement of the linkage.

21. An apparatus according to claim 20, wherein the blocking member is operatively connected to the guide member.

22. An apparatus according to claim 19, wherein the second locking mechanism includes a shuttle member positioned within the handle portion, the shuttle member being movable to a position substantially preventing movement of the linkage.

23. An apparatus according to claim 22, wherein the second locking mechanism further includes a blocking segment operatively connected to the guide member and movable therewith, the blocking segment being movable from the first position to the second position to move the shuttle member to the position substantially preventing movement of the linkage.

24. An apparatus for applying surgical staples comprising:
a frame including a stationary jaw;
a movable jaw supported on the frame, the movable jaw being movable into approximation with the stationary jaw;
a cartridge containing a plurality of staples supported on one of the stationary jaw and the movable jaw and an anvil supported on the other of the stationary jaw and the movable jaw;
a guide member movably supported on the frame from a retracted position to an advanced position to maintain the relative alignment of the stationary jaw and the movable jaw;
a first locking mechanism operatively associated with the guide member, the first locking mechanism being movable to a position to prevent movement of the guide member to the advanced position; and
an operating member supported within the apparatus, the operating member being movable from a proximal position to a distal position to effect ejection of the plurality of staples.

25. An apparatus according to claim 24, wherein the first locking mechanism is supported on the movable jaw.

26. An apparatus according to claim 24, wherein the guide member includes an elongated pin having a guideway formed therein, the first locking mechanism being movable into the guideway to prevent movement of the elongated pin to the advanced position.

27. An apparatus according to claim 26, wherein the first locking mechanism includes a platform having a channel formed therein and a first member movably positioned within the channel from an unlocked position to a locked position, wherein in the locked position the locking mechanism extends into the guideway.

28. An apparatus according to claim 27, wherein the first locking mechanism further includes a cooperating member movably positioned within the channel, the cooperating member being operatively associated with the first member such that when the first member is in the unlocked position, the cooperating member is spaced from the guide member, and when the first member is in the locked position, the cooperating member operatively extends into the guideway.

29. An apparatus according to claim 27, further including at least one pusher member operatively associated with the operating member, the pusher member being movable from a loaded position to a fired position to effect ejection of the plurality of staples.

30. An apparatus according to claim 29, wherein when the pusher member is in the loaded position, the pusher member engages the first member of the first locking mechanism to retain the first member in the unlocked position.

31. An apparatus according to claim 30, wherein the first locking member further includes a biasing member positioned within the channel, the biasing member being positioned to bias the first member to the locked position, such that when the pusher member is moved to the fired position, the first member is biased to the locked position by the biasing member.

32. An apparatus according to claim 24, wherein the cartridge is removable and the first locking mechanism is supported on the removable cartridge.

33. An apparatus according to claim 32, wherein the cartridge includes a guide bore, the guide member being movable though the guide bore during approximation of the movable jaw and the stationary jaw.

34. An apparatus according to claim 33, wherein the first locking mechanism includes an interference member, the interference member being movable from a first position permitting passage of the guide member through the guide bore to a second position blocking passage of the guide member through the guide bore.

35. An apparatus according to claim 34, further including a biasing member, the biasing member urging the interference member to the second position.

36. An apparatus according to claim 35, further including at least one pusher member operatively associated with the operating member, the at least one pusher member being movable from a loaded position to a fired position in response to movement of the operating member from the proximal position to the distal position to effect ejection of the plurality of staples.

37. An apparatus according to claim 36, wherein when the at least one pusher member is in the loaded position, the at least one pusher member operatively engages the interference member to retain the interference member in the first position.

\* \* \* \* \*